United States Patent
Liebeschuetz et al.

(10) Patent No.: US 6,784,182 B2
(45) Date of Patent: Aug. 31, 2004

(54) SERINE PROTEASE INHIBITORS

(75) Inventors: John Walter Liebeschuetz, Bollington (GB); Christopher William Murray, Swavesey (GB); Stephen Clinton Young, Heaton Moor (GB); Nicholas Paul Camp, Bracknell (GB); Stuart Donald Jones, Macclesfield (GB); William Alexander Wylie, Carrickfergus (GB); John Joseph Masters, Fishers, IN (US); Michael Robert Wiley, Indianapolis, IN (US); Scott Martin Sheehan, Carmel, IN (US); David Birenbaum Engel, Bloomington, IN (US); Brian Morgan Watson, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 152 days.

(21) Appl. No.: 10/030,186
(22) PCT Filed: Jun. 12, 2001
(86) PCT No.: PCT/GB01/02572
§ 371 (c)(1), (2), (4) Date: Feb. 4, 2002
(87) PCT Pub. No.: WO01/96304
PCT Pub. Date: Dec. 20, 2001

(65) Prior Publication Data
US 2002/0151724 A1 Oct. 17, 2002

(30) Foreign Application Priority Data
Jun. 13, 2000 (WO) .............................. PCT/GB00/02302
Dec. 13, 2000 (GB) ................................................. 0030306

(51) Int. Cl.[7] ..................... C07D 211/26; C07D 401/12; C07D 403/12; A61K 31/445; A61P 7/02
(52) U.S. Cl. .................. 514/253.09; 546/201; 546/245; 546/208; 546/187; 546/189; 546/193; 514/323; 514/330; 514/326; 514/316; 514/318; 544/364
(58) Field of Search ................................ 546/201, 245, 546/208, 187, 189, 193; 514/323, 330, 326, 316, 253.09, 318; 544/364

(56) References Cited

U.S. PATENT DOCUMENTS

| | | | |
|---|---|---|---|
| 5,346,907 A | 9/1994 | Kerwin et al. | |
| 6,545,055 B1 | 4/2003 | Zhu et al. | |

FOREIGN PATENT DOCUMENTS

| | | | |
|---|---|---|---|
| EP | 796866 A1 | 9/1997 | |
| WO | WO 91/00725 | 1/1991 | |
| WO | WO 97/49404 | 12/1997 | |
| WO | WO 98/47876 | 10/1998 | |
| WO | WO 99/00121 | 1/1999 | |
| WO | WO 99/00126 | 1/1999 | |
| WO | WO 99/00127 | 1/1999 | |
| WO | WO 99/00128 | 1/1999 | |
| WO | WO 99/11657 | 3/1999 | |
| WO | WO 9911657 A1 * | 3/1999 | ............ C07K/5/06 |
| WO | WO 99/11658 | 3/1999 | |
| WO | WO 00/39092 | 7/2000 | |
| WO | WO 00/39111 | 7/2000 | |
| WO | WO 00/39117 | 7/2000 | |
| WO | WO 00/39118 | 7/2000 | |
| WO | WO 00/71493 | 11/2000 | |
| WO | WO 00/71507 | 11/2000 | |
| WO | WO 00/71508 | 11/2000 | |
| WO | WO 00/76970 | 12/2000 | |
| WO | WO 00/76971 | 12/2000 | |
| WO | WO 00/77027 | 12/2000 | |

OTHER PUBLICATIONS

Jones, Stuart D, et al., Bioorganic & Medicinal Chemistry Letters 11 (2001) 733–736.

* cited by examiner

Primary Examiner—Mukund J. Shah
Assistant Examiner—Hong Liu
(74) Attorney, Agent, or Firm—Martin A. Hay

(57) ABSTRACT

Compounds of formula (I)

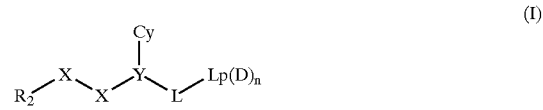

in which $R_2$, X, Y, Cy, L and $Lp(D)_n$ have the meanings given in the specification, are inhibitors of the serine protease, factor Xa and are useful in the treatment of cardiovascular disorders.

18 Claims, No Drawings

SERINE PROTEASE INHIBITORS

This invention relates to compounds which are inhibitors of serine proteases, to pharmaceutical compositions thereof and to their use in the treatment of the human or animal body.

The serine proteases are a group of proteolytic enzymes which have a common catalytic mechanism characterized by a particularly reactive Ser residue. Examples of serine proteases include trypsin, tryptase, chymotrypsin, elastase, thrombin, plasmin, kallikrein, Complement C1, acrosomal protease, lysosomal protease, cocoonase, α-lytic protease, protease A, protease B, serine carboxypeptidase II, subtilisin, urokinase, Factor VIIa, Factor IXa, and Factor Xa. The serine proteases have been investigated extensively over a period of several decades and the therapeutic value of inhibitors of serine proteases is well understood.

Serine protease inhibitors play a central role in the regulation of a wide variety of physiological process including coagulation, fibrinolysis, fertilization, development, malignancy, neuromuscular patterning and inflammation. It is well known that these compounds inhibit a variety of circulating proteases as well as proteases that are activated or released in tissue. It is also becoming clear that serine protease inhibitors inhibit critical cellular processes, such as adhesion, migration, free radical production and apoptosis. In addition, animal experiments indicate that intravenously administered serine protease inhibitors, variants or cells expressing serine protease inhibitors, provide a protective effect against tissue damage.

Serine protease inhibitors have also been predicted to have potential beneficial uses in the treatment of disease in a wide variety of clinical areas such as oncology, neurology, haematology, pulmonary medicine, immunology, inflammation and infectious disease.

In particular serine protease inhibitors may be beneficial in the treatment of thrombotic diseases, asthma, emphysema, cirrhosis, arthritis, carcinoma, melanoma, restenosis, atheroma, trauma, shock and reperfusion injury.

Thus for example an inhibitor of Factor Xa has value as a therapeutic agent as an anticoagulant, e.g. in the treatment and prevention of thrombotic disorders. The use of a Factor Xa inhibitor as an anticoagulant is desirable in view of the selectivity of its effect. Many clinically approved anticoagulants have been associated with adverse events owing to the non-specific nature of their effects on the coagulation cascade.

Also, there are well-known associations of α1 protease inhibitor deficiency with emphysema and cirrhosis and C1 esterase inhibitor deficiency with angioedema.

It has now been found that certain aromatic compounds are particularly effective as inhibitors of serine proteases, especially proteases with negatively charged P1 specificity pockets, and most especially the serine protease Factor Xa. The Factor Xa inhibitors of this invention are potentially useful for the prophylaxis or treatment of thrombotic disorders such as amongst others venous thrombosis, pulmonary embolism, arterial thrombosis, myocardial ischaemia, myocardial infarction, and cerebral thrombosis. They potentially have benefit in the treatment of acute vessel closure associated with thrombolytic therapy and restenosis, e.g. after transluminal coronary angioplasty or bypass grafting of the coronary or peripheral arteries and in the maintenance of vascular access patency in long term hemodialysis patients.

Factor Xa inhibitors of this invention may, with benefit, form part of a combination therapy with an anticoagulant with a different mode of action or with a thrombolytic agent.

It has been reported in WO99/11658 and WO99/11657 that certain benzamidine and aminoisoquinoline derivatives carrying a bulky lipophilic side chain are excellent inhibitors of serine proteases. Unfortunately, it has since been found that benzamidine compounds of WO 99/11658 in general demonstrate poor oral bioavailability.

Surprisingly, it has now been found that certain other aromatic compounds also show inhibitory activity against serine proteases, in particular Factor Xa, despite the lack of the amidino or 1-aminoisoquinoline functionality previously believed to be crucial for activity as a factor Xa inhibitor. Many of these compounds also possess other structural features that further distinguish them from the compounds of WO99/11658 and WO99/11657.

Where compounds of the invention have been tested, they have generally demonstrated superior oral bioavailability in comparison with benzamidines disclosed in WO 99/11658. Also, it has been found that the compounds of the invention perform excellently in the prothrombin time assay (PT) when compared to aminoisoquinolines of similar factor Xa activity and structure. The PT assay is a coagulation assay and it is widely accepted that direct acting Factor Xa inhibitors which perform well in the PT assay are more likely to be good antithrombotics. Compounds of the invention have also been found to exhibit a good duration of action following oral administration.

In WO99/09053 certain 2-aminobenzamide compounds are disclosed as potential motilin receptor antagonists and in U.S. Pat. No. 3,268,513 similar 2-aminobenzamide compounds are suggested as potential antibacterial agents. However, the novel compounds of the present invention have not before been suggested as potential serine protease inhibitors.

Thus viewed from an one aspect the invention provides a serine protease inhibitor compound of formula (I)

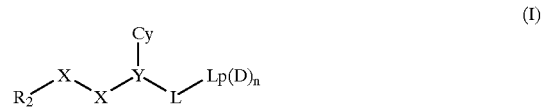

(I)

wherein:

$R_2$ is a 5 or 6 membered aromatic carbon ring optionally interrupted by a nitrogen, oxygen or sulphur ring atom, optionally being substituted in the 3 and/or 4 position (in relation to the point of attachment of X—X) by halo, nitro, thiol, haloalkoxy, hydrazido, alkylhydrazido, amino, cyano, haloalkyl, alkylthio, alkenyl, alkynyl, acylamino, tri or difluoromethoxy, carboxy, acyloxy, $MeSO_2$— or $R_1$, or the substituents at the 3 and 4 positions taken together form a fused ring which is a 5 or 6 membered carbocyclic or heterocyclic ring optionally substituted by halo, haloalkoxy, haloalkyl, cyano, nitro, amino, hydrazido, alkylthio, alkenyl, alkynyl or $R_{1j}$, and optionally substituted in the position alpha to the X—X group (i.e. 6 position for a six membered aromatic ring etc) by amino, hydroxy, halo, alkyl, carboxy, alkoxycarbonyl, cyano, amido, aminoalkyl, alkoxy or alkylthio with the proviso that $R_2$ cannot be aminoisoquinolyl;

each X independently is a C, N, O or S atom or a CO, $CR_{1a}$, $C(R_{1a})_2$ or $NR_{1a}$ group, at least one X being C, CO, $CR_{1a}$ or $C(R_{1a})_2$;

each $R_{1a}$ independently represents hydrogen or hydroxyl, alkoxy, alkyl, aminoalkyl, hydroxyalkyl alkoxyalkyl, alkoxycarbonyl, alkylaminocarbonyl, alkoxycarbonylamino, acyloxymethoxycarbonyl or alkylamino optionally substituted by hydroxy, alkylamino, alkoxy, oxo, aryl or cycloalkyl;

$R_1$ is as defined for $R_{1a}$, provided that $R_1$ is not unsubstituted aminoalkyl;

Y (the α-atom) is a nitrogen atom or a $CR_{1b}$ group;

Cy is a saturated or unsaturated, mono or poly cyclic, homo or heterocyclic group, preferably containing 5 to 10 ring atoms and optionally substituted by groups $R_{3a}$ or phenyl optionally substituted by $R_{3a}$ or $R_{3i}X_i$;

each $R_{3a}$ independently is $R_{1c}$, amino, halo, cyano, nitro, thiol, alkylthio, alkylsulphonyl, alkylsulphenyl, triazolyl, imidazolyl, tetrazolyl, hydrazido, alkylimidazolyl, thiazolyl, alkylthiazolyl, alkyloxazolyl, oxazolyl, alkylsulphonamido, alkylaminosulphonyl, aminosulphonyl, haloalkoxy, haloalkyl, a group of the formula —$C(X^3)N(R^{11})R^{12}$ (wherein $X^3$ is O or S; and $R^{11}$ and $R^{12}$ are independently selected from hydrogen, methyl or ethyl or together with the nitrogen atom to which they are attached form a pyrrolidin-1-yl, piperidin-1-yl or morpholino group), or —$OCH_2O$— which is bonded to two adjacent ring atoms in Cy;

$X_i$ is a bond, O, NH or $CH_2$;

$R_{3i}$ is phenyl pyridyl or pyrimidinyl optionally substituted by $R_{3a}$;

$R_{1b}$, $R_{1c}$ and $R_{1j}$ are as defined for $R_{1a}$; and
—L—Lp(D)$_n$ is

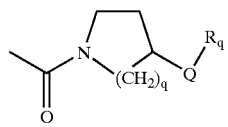

q is 1 or 2;

Q is methylene; and $R_q$ is $NR_aR_b$ in which each of $R_a$ and $R_b$ independently is hydrogen or $C_{1-3}$alkyl; or one of $R_a$ and $R_b$ is hydrogen or methyl and the other of $R_a$ and $R_b$ is (3–6C) cycloalkyl, pyrid-4-yl, —$CH_2$—$R_c$ or —$CH_2$—$R_d$ in which $R_c$ is pyridyl or phenyl (which phenyl may bear a fluoro, chloro, methyl, $CONH_2$, $SO_2NH_2$, methylaminosulphonyl, dimethylaminosulphonyl, methylsulphonylamino, methoxy or methylsulphonyl substituent) and in which $R_d$ is isopropyl or cyclopentyl, or $NR_aR_b$ is azetidino, pyrrolidino, piperidino, morpholino, thiomorpholino, piperazino, or tetrahydro-1,4-diazepino [in which a pyrrolidino or piperidino may be a 3,4-didehydro derivative and in which a azetidino, pyrrolidino, piperidino, morpholino, thiomorpholino, piperazino, or tetrahydro-1,4-diazepino may be optionally substituted on a ring carbon atom by hydroxy, amino, (1–3C)alkoxy, (1–3C)hydroxyalkyl, (1–3C)alkyl, carboxy, methoxycarbonyl or ethoxycarbonyl (provided that the amino, hydroxy or alkoxy substituent is not on a ring carbon atom which is included in a double bond, or adjacent to a ring oxygen, sulfur or nitrogen atom) and in which the piperazino or tetrahydro-1,4-diazepino may bear a methyl group at the 4-position];

or a physiologically-tolerable salt thereof, e.g. a halide, phosphate or sulphate salt or a salt with ammonium or an organic amine such as ethylamine or meglumine. In the compounds of the invention, where the alpha atom is carbon it preferably has the conformation that would result from construction from a D-α-aminoacid $NH_2$—$CR_{1b}$(Cy)—COOH where the $NH_2$ represents part of X—X. Likewise the fourth substituent $R_{1b}$ at an alpha carbon is preferably a methyl or hydroxymethyl group or hydrogen. It will be appreciated that the compounds of formula (I) may exist in racemic or chiral form, and that the preferred D-isomer may be administered in a racemic mixture with the L-isomer, or alone.

In the compounds of the invention, unless otherwise indicated, aryl groups preferably contain 5 to 10 ring atoms optionally including 1, 2 or 3 heteroatoms selected from O, N and S; alkyl, alkenyl or alkynyl groups or alkylene moieties preferably contain up to 6 carbons, e.g. $C_{1-6}$ or $C_{1-3}$; cyclic groups preferably have ring sizes of 3 to 8 atoms; and fused multicyclic groups preferably contain 8 to 16 ring atoms.

Examples of particular values for $R_{1a}$ are: hydrogen, methyl or ethyl. $R_{1a}$ is preferably a hydrogen atom.

The linker group from the $R_2$ group to the alpha atom is preferably selected from —CH=CH—, —CONH—, —$CONR_{1a}$—, —NH—CO—, —NH—$CH_2$—, —$CH_2$—NH—, —$CH_2O$—, —$OCH_2$—, —COO—, —OC=O— and —$CH_2CH_2$—. Preferably, the X moiety nearest to the alpha atom is an NH or O atom, most preferably a NH group. The X moiety alpha to the aromatic ring is preferably a carbon based group such as $CH_2$ or CO, preferably CO. Thus a particularly preferred linker X—X is —CONH—. In an alternative embodiment the linker is preferably a —$OCH_2$— group.

Examples of particular values for $R_{1b}$ are: hydrogen, (1–4C)alkyl, such as methyl or hydroxy (1–4C)alkyl, such as hydroxymethyl. $R_{1b}$ is preferably a hydrogen atom.

The alpha atom (Y) is preferably a CH or C($CH_3$) group, especially CH.

In the group —L—Lp(D)$_n$, preferably the azetidino, pyrrolidino, piperidino, morpholino, thiomorpholino, piperazino or tetrahydro-1,4-diazepino in $NR_aR_b$ is optionally substituted on a ring carbon atom by methyl, hydroxy or hydroxymethyl.

A preferred sub-group of compounds of formula I is that in which wherein —L—Lp(D)$_n$ is of the formula:

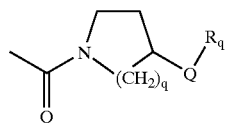

wherein:

q is 1 or 2;

Q is methylene; and $R_q$ is $NR_aR_b$ in which each of $R_a$ and $R_b$ independently is hydrogen or $C_{1-3}$alkyl; or one of $R_a$ and $R_b$ is hydrogen or methyl and the other of $R_a$ and $R_b$ is —$CH_2$—$R_c$ or —$CH_2$—$R_d$ in which $R_c$ is pyridyl or phenyl (which phenyl may bear a fluoro, chloro, methyl, $CONH_2$, $SO_2NH_2$, methylaminosulphonyl, dimethylaminosulphonyl, methylsulphonylamino, methoxy or methylsulphonyl substituent) and in which $R_d$ is isopropyl or cyclopentyl, or $NR_aR_b$ is pyrrolidino, piperidino, morpholino, piperazino, or tetrahydro-1,4-diazepino in which a pyrrolidino or piperidino may be a 3,4-didehydro derivative and in which a pyrrolidino, piperidino, piperazino, or tetrahydro-1,4-diazepino may bear a ethyl group at the 4-position.

q is preferably 2.

Preferably —L—Lp(D)$_n$ is of the formula:

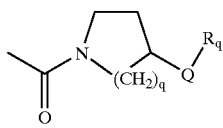

wherein:
q is 1 or 2;
Q is methylene; and R$_q$ is NR$_a$R$_b$ in which each of R$_a$ and R$_b$ independently is hydrogen or C$_{1-3}$alkyl; or one of R$_a$ and R$_b$ is hydrogen and the other is (3–6C)cycloalkyl or pyrid-4-yl; or NR$_a$R$_b$ is azetidino, pyrrolidino, piperidino or piperazino [in which a pyrrolidino or piperidino may be a 3,4-didehydro derivative and in which a azetidino, pyrrolidino, piperidino or piperazino may be optionally substituted on a ring carbon atom by methyl, hydroxy or hydroxymethyl (provided that the hydroxy substituent is not on a ring carbon atom which is included in a double bond, or adjacent to a ring nitrogen atom) and in which the piperazino may bear a methyl group at the 4-position].

More preferably R$_q$ is selected from dimethylamino, diethylamino, prop-2-ylamino, pyrrolidino, 3-pyrrolino, 3-hydroxypyrrolidino, 3-hydroxymethylpyrrolidino, piperidino, 3-hydroxypiperidino, 4-hydroxypiperidino, 4-hydroxymethyl-piperidino, piperazino and 4-methylpiperazino.

Examples of particular values for R$_q$ are dimethylamino, diethylamino, prop-2-ylamino, pyrrolidino, 3-pyrrolino, 3-hydroxypyrrolidino, 3-hydroxymethylpyrrolidino, 3(S)-hydroxypyrrolidino, 3(S)-hydroxymethylpyrrolidino, 3(R)-hydroxymethylpyrrolidino, piperidino, 4-hydroxypiperidino, 4-hydroxymethylpiperidino, 3-hydroxypiperidino, piperazino and 4-methylpiperazino.

When R$_a$ or R$_b$ represents a C$_{1-3}$ alkyl group, this may be, for example, a methyl or ethyl group. When R$_b$ represents a C$_{3-6}$cycloalkyl group, this may be, for example, a cyclohexyl group.

Preferably R$_q$ is NR$_a$R$_b$ in which R$_a$ is hydrogen or C$_{1-3}$alkyl and R$_b$ is C$_{1-3}$alkyl; or R$_a$ is hydrogen and R$_b$ is (3–6C)cycloalkyl or pyrid-4-yl; or NR$_a$R$_b$ is azetidino, pyrrolidino, piperidino, morpholino, thiomorpholino or piperazino [in which a pyrrolidino, piperidino or piperazino may be optionally substituted on a ring carbon atom by hydroxy or hydroxymethyl (provided that the hydroxy substituent is not on a ring carbon atom which is adjacent to a ring nitrogen atom) and in which the piperazino may bear a methyl group at the 4-position].

Most preferably, the group L—Lp(D)$_n$ is selected from

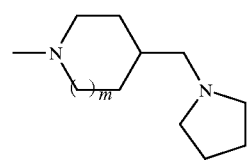

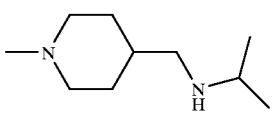

-continued

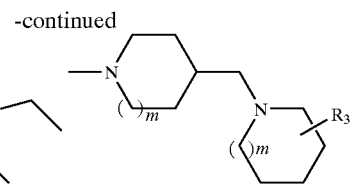

wherein:
m represents 0 or 1;
and when R$_3$ is present as a substituent on a saturated ring, it is selected from hydrogen, hydroxy, amino, (1–3C)alkoxy, (1–3C)hydroxyalkyl, (1–3C)alkyl, carboxy, methoxycarbonyl and ethoxycarbonyl.

For example specific groups of formula L—Lp(D)$_n$ include

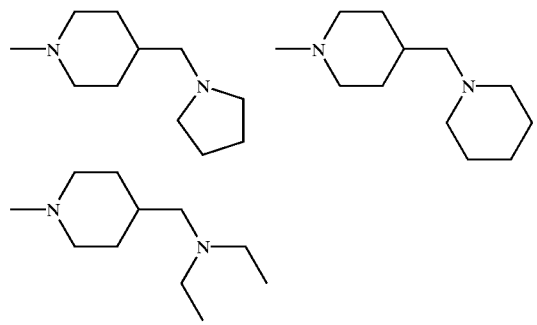

Cy is preferably an optionally R$_{3a}$ substituted: phenyl, pyridyl, thienyl, thiazolyl, naphthyl, piperidinyl, furanyl, pyrrolyl, isoxazolyl, isothiazolyl, pyrazolyl, oxazolyl, imidazolyl, 1,2,4-thiadiazolyl, 1,3,4-thiadiazolyl, pyrimidinyl, pyridazinyl, quinoloyl, isoquinolyl, benzofuryl, benzothienyl or cycloalkyl group, or a phenyl group substituted by R$_{3i}$X$_i$ in which X$_i$ is a bond, O, NH or CH$_2$ and R$_{3i}$ is phenyl, pyridyl or pyrimidinyl optionally substituted by R$_{3a}$.

The cyclic group attached to the alpha carbon may thus be an optionally R$_{3a}$ substituted phenyl, pyridyl (such as pyrid-2-yl, pyrid-3-yl or pyrid-4-yl), thienyl (such as thien-2-yl or thien-3-yl), thiazolyl (such as thiazol-2-yl, thiazol-4-yl or thiazol-5-yl), naphthyl (such as naphth-1-yl), piperidinyl (such as piperidin-4-yl) or cycloalkyl, such as a cyclohexyl group.

Examples of values for Cy when it represents phenyl substituted by R$_{3i}$X$_i$ are 3-(2-pyridyl)phenyl, 3-(3-pyridylphenyl and 3-(4-pyridylphenyl).

Examples of particular values for R$_{3a}$ are:
hydrogen;
hydroxyl;
for alkoxy: methoxy or ethoxy;
for alkyl optionally substituted by hydroxy, alkylamino, alkoxy, oxo, aryl or cycloalkyl: alkyl, such as methyl or ethyl, or alkylaminoalkyl, such as methylaminomethyl or dimethylaminomethyl;
for hydroxyalkyl optionally substituted by hydroxy, alkylamino, alkoxy, oxo, aryl or cycloalkyl: hydroxymethyl or carboxy;
for alkoxyalkyl: methoxymethyl;
for alkoxycarbonyl: methoxycarbonyl or ethoxycarbonyl;
for alkylaminocarbonyl: methylaminocarbonyl or dimethylaminocarbonyl;
for aminoalkyl optionally substituted by hydroxy, alkylamino, alkoxy, oxo, aryl or cycloalkyl: aminomethyl, CONH$_2$ or CH$_2$CONH$_2$; for alkylamino optionally substituted by hydroxy, alkylamino, alkoxy, oxo, aryl or cycloalkyl: (1–6C)alkanoylamino, such as acetylamino;
for alkoxycarbonylamino: methoxycarbonylamino, ethoxycarbonylamino or t-butoxycarbonylamino; amino;
for halo: fluoro, chloro or bromo;
cyano;
nitro;
thiol;
for alkylthio: methylthio;
for alkylsulphonyl: methylsulphonyl or ethylsulphonyl;
for alkylsulphenyl: methylsulphenyl;
for alkylsulphonamido: methylsulphonylamido or ethylsulphonylamido;
for alkylaminosulphonyl: methylaminosulphonyl or ethylaminosulphonyl;
aminosulphonyl;
for haloalkoxy: trifluoromethoxy;
for haloalkyl: trifluoromethyl;
for a group of formula —C(X$^3$)N(R$^{11}$)R$^{12}$: pyrrolidin-1-ylcarbonyl, piperidin-1-ylcarbonyl or morpholin-1-ylcarbonyl; and —OCH$_2$O— which is bonded to two adjacent ring atoms in Cy.
Examples of particular values for R$_{1c}$ are:
hydrogen;
hydroxyl;
for alkoxy: methoxy or ethoxy;
for alkyl optionally substituted by hydroxy, alkylamino, alkoxy, oxo, aryl or cycloalkyl: alkyl, such as methyl or ethyl, or alkylaminoalkyl, such as methylaminomethyl or dimethylaminomethyl;
for hydroxyalkyl: hydroxymethyl;
for alkoxyalkyl: methoxymethyl;
for alkoxycarbonyl: methoxycabonyl or ethoxycarbonyl;
for alkylaminocarbonyl: methylaminocarbonyl or dimethylaminocarbonyl;
for alkoxycarbonylamino: methoxycarbonylamino, ethoxycarbonylamino or t-butoxycarbonylamino;
for alkylamino optionally substituted by hydroxy, alkylamino, alkoxy, oxo, aryl or cycloalkyl: (1–6C) alkanoylamino, such as acetylamino; and
for aminoalkyl substituted by hydroxy, alkylamino, alkoxy, oxo, aryl or cycloalkyl: aminomethyl, CONH$_2$ or CH$_2$CONH$_2$.
Preferably R$_{3a}$ is hydrogen, hydroxyl, methoxy, methyl, amino, fluoro, chloro, ethylsulphonylamino, amido or methylaminocarbonyl.
Examples of values for R$_{3i}$ are phenyl, pyrid-2-yl, pyrid-3-yl, pyrid-4-yl pyrimid-2-yl and pyrimid-6-yl.
Examples of particular values for Cy are phenyl, 4-aminophenyl, 4-amidophenyl, 4-(N-methyl)amidophenyl, 4-(N,N-dimethyl)amidophenyl, 2-chlorophenyl, 2-methylphenyl, 2-fluorophenyl, 3-fluorophenyl, 4-fluorophenyl, 4-hydroxphenyl, 2-methoxyphenyl, 4-methoxyphenyl, 4-carboxyphenyl, 3-ethylsulphonylaminophenyl, thien-2-yl, thien-3-yl, thiazol-4-yl, thiazol-5-yl, 2-methylthiazol-4-yl, pyrid-2-yl, pyrid-3-yl, pyrid-4-yl, piperidin-4-yl, 1-methylpiperidin-4-yl, cyclohexyl and naphth-1-yl. Other examples are: 4-carbamoylphenyl; furan-2-yl; furan-3-yl; imidazol-2-yl; thiazol-2-yl; 2-aminothiazol-4-yl; isoquinolin-5-yl; isoquinolin-8-yl; quinolin-5-yl; and quinolin-8-yl. Further examples are: 2-trifluoromethylphenyl; 2-methylthiophenyl; 2-methylsulfonylphenyl; 3-bromophenyl; 3-cyanophenyl; and benzo[b]thiophen-3-yl.

Particular mention is made of the following values for Cy:

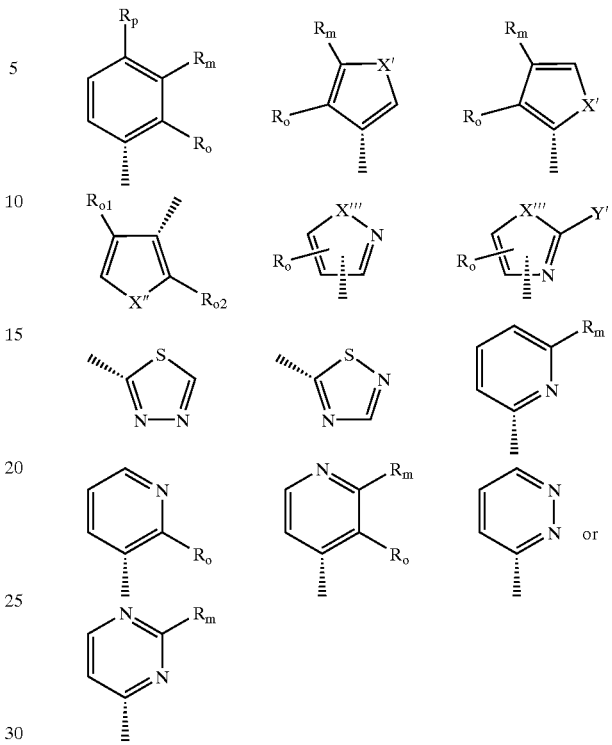

wherein:
X' is selected from O, S and NMe;
X" is selected from O and S;
X'" is selected from O, S, NH and NMe;
Y' is selected from hydrogen, amino and methyl;
R$_o$ is selected from hydrogen, methyl, fluoro, chloro, trifluoromethyl, methoxy, methylthio, methylsulphinyl and methylsulphonyl;
R$_m$ is selected from hydrogen, methyl, fluoro, chloro, trifluoromethyl, methoxy, methylthio, methylsulphinyl, methylsulphonyl, carboxy, methoxycarbonyl and a group of the formula —C(X$^3$)N(R$^{11}$)R$^{12}$ (wherein X$^3$ is O or S, and R$^{11}$ and R$^{12}$ are independently selected from hydrogen, methyl or ethyl or together with the nitrogen atom to which they are attached form a pyrrolidin-1-yl, piperidin-1-yl or morpholino group);
R$_p$ is selected from hydrogen and fluoro; or
R$_o$ and R$_m$ and R$_m$ and R$_p$ form an —OCH2O— group; or
R$_o$ and R$_m$ together with the ring to which they are attached form a 5 or 6 membered aryl or heteroaryl ring (wherein the heteroary ring contains 1 or 2 heteroatoms selected from nitrogen, oxygen and sulfur); and
one of R$_{o1}$ and R$_{o2}$ is hydrogen and the other is R$_o$.
Preferably Cy is selected from phenyl (optionally substituted by ethyl, prop-2-yl, phenoxy, hydroxy, ethoxy, benzyloxy, prop-2-yloxy, nitro, amino, acetylamino, methylsufonylamino, dimethylamino, chloro, methoxy, trifluoromethyl, methylthio, methylsulfonyl, tert-butylthio, tert-butylsulfonyl, aminosulfonyl or carbamoyl), pyridyl, thienyl, furanyl, imidazolyl, thiazolyl (optionally substituted by amino or methyl), napththyl, isoquinolinyl and quinolinyl.
Examples of values for Cy when it represents thiazolyl substituted by amino or methyl are 2-aminothiazol-4-yl and 2-methylthiazol-4-yl.
Preferably Cy is selected from phenyl, 2-chlorophenyl, 2-methoxyphenyl, 4-carbamoylphenyl, pyrid-2-yl, pyrid-4- yl, thien-2-yl, thien-3-yl, furan-2-yl, furan-3-yl, imidazol-2-yl, thiazol-2-yl, thiazol-4-yl, 2-amino-thiazol-4-yl, thiazol-5-yl, naph-1-thyl, isoquinolin-5-yl, isoquinolin-8-yl, quinolin-4-yl, quinolin-5-yl and quinolin-8-yl.

More preferably Cy is selected from phenyl, 2-methoxyphenyl, 4-carbamoylphenyl, pyrid-2-yl, thien-2-yl, thien-3-yl, furan-2-yl, furan-3-yl, imidazol-2-yl, thiazol-2-yl, thiazol-4-yl, thiazol-5-yl and quinolin-4-yl.

A value for Cy of particular interest is phenyl.

Referring to the group $R_2$, examples of a 5 or 6 membered aromatic carbon ring optionally interrupted by a nitrogen, oxygen or sulphur ring atom are phenyl; pyrrolyl, such as 2-pyrrolyl; pyridyl, such as 3-pyridyl; pyrazinyl, such as 2-pyrazinyl; furyl, such as 2-furyl; and thienyl, such as 2-thienyl or 3-thienyl. Preferably the ring is interrupted (i.e. a carbon atom is replaced) by at most one heteroatom. More preferably the ring is phenyl, 2-thienyl or 2-pyrrolyl. Most preferably, the ring is phenyl.

When the ring is phenyl, the group $R_2$ may be a group of formula

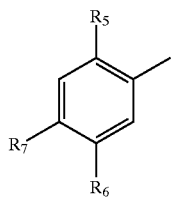

in which $R_5$ is amino, hydroxy or hydrogen, and $R_6$ and $R_7$ which may be the same or different represent halo, nitro, thiol, cyano, haloalkyl, haloalkoxy, amido, hydrazido, amino, alkylthio, alkenyl, alkynyl or $R_1$ or taken together form a 5 or 6 membered fused carbocyclic ring or 5 membered heterocyclic ring, which may itself be substituted by $R_{1j}$, amino, halo, cyano, nitro, thiol, alkylthio, haloalkyl, haloalkoxy.

When the substituents at the 3 and 4 positions taken together form a fused ring which is a 5 or 6 membered carbocyclic or heterocyclic ring, examples of the resultant bicyclic ring are naphthyl, such as 2-naphthyl; benzimidazolyl, such as benzimidazol-5-yl or benzimidazol-6-yl; isoquinolinyl, such as isoquinolin-7-yl; indolyl, such as indol-2-yl, indol-5-yl or indol-6-yl; indazolyl, such as indazol-5-yl; indazol-6-yl; 3,4-methylenedioxyphenyl; dihydroindolyl, such as 2,3-dihydroindol-6-yl; benzothiazolyl, such as benzothiazol-2-yl or benzothiazol-6-yl; benzo[b]thiophenyl, such as benzo[b]thiophen-2-yl; benzofuryl, such as benzofur-2-yl; imidazo[1,2-a]pyrimidinyl, such as imidazo[1,2-a]pyrimidin-2-yl; tetrahydroimidazo[1,2-a]pyrimidinyl, such as tetrahydroimidazo[1,2-a]pyrimidin-2-yl; and benzisoxazolyl, such as benzisoxazol-5-yl.

Preferably $R_2$ is phenyl, thien-2-yl, naphthyl, indol-2-yl, indol-6-yl, benzo[b]furan-5-yl, benzo[b]thiophen-2-yl or benzimidazol-2-yl, optionally substituted as defined hereinabove.

$R_2$ preferably represents:

(i) phenyl optionally being substituted in the 3 and/or 4 position by halo, nitro, thiol, haloalkoxy, hydrazido, alkylhydrazido, amino, cyano, haloalkyl, alkylthio, alkenyl, alkynyl, acylamino, tri or difluoromethoxy, carboxy, acyloxy, $MeSO_2$— or $R_1$, and optionally substituted at the 6 position by amino, hydroxy, halo, alkyl, carboxy, alkoxycarbonyl, cyano, amido, aminoalkyl, alkoxy or alkylthio;

(ii) naphth-2-yl optionally substituted at the 6 or 7 position by halo, haloalkoxy, haloalkyl, cyano, nitro, amino, hydrazido, alkylthio, alkenyl, alkynyl or $R_{1j}$ and optionally substituted at the 3 position by amino, hydroxy, halo, alkyl, carboxy, cyano, amido, aminoalkyl, alkoxy or alkylthio;

(iii) isoquinolin-7-yl, indol-5-yl, indol-6-yl, indazol-5-yl, indazol-6-yl, benzothiazol-6-yl or benzisoxazol-5-yl optionally substituted at the 3 position by halo, haloalkoxy, haloalkyl, cyano, nitro, amino, hydrazido, alkylthio, alkenyl, alkynyl or $R_{1j}$;

(iv) benzimidazol-5-yl or benzothiazol-6-yl optionally substituted at the 2 position by amino;

(v) thien-2-yl or thien-3-yl optionally substituted at the 4 or 5 position by halo, haloalkoxy, haloalkyl, cyano, nitro, amino, hydrazido, alkylthio, alkenyl, alkynyl or $R_1$;

(vi) 3,4-methylenedioxyphenyl, 2,3-dihydroindol-6-yl, 3,3-dichloro-2-oxo-indol-6-yl or 1-methyl-3-aminoindazol-5-yl;

(vii) benzothiazol-2-yl, imidazo[1,2-a]pyrimidin-2-yl or tetrahydroimidazo[1,2-a]pyrimidin-2-yl;

(viii) pyrazol-2-yl optionally substituted at the 5 position by halo, haloalkoxy, haloalkyl, cyano, nitro, amino, hydrazido, alkylthio, alkenyl, alkynyl or $R_1$;

(ix) pyrid-2-yl optionally substituted at the 5 position by halo, haloalkoxy, haloalkyl, cyano, nitro, amino, hydrazido, alkylthio, alkenyl, alkynyl or $R_1$;

(x) pyrid-3-yl optionally substituted at the 6 position by halo, haloalkoxy, haloalkyl, cyano, nitro, amino, hydrazido, alkylthio, alkenyl, alkynyl or $R_1$;

(xi) benzofur-2-yl optionally substituted at the 3 position by amino, hydroxy, halo, alkyl, carboxy, cyano, amido, aminoalkyl, alkoxy or alkylthio and at the 5 or 6 position by halo, haloalkoxy, haloalkyl, cyano, nitro, amino, hydrazido, alkylthio, alkenyl, alkynyl or $R_{1j}$;

(xii) indol-2-yl optionally substituted on the indole nitrogen atom by alkyl and optionally substituted at the 5 or 6 position by halo, haloalkoxy, haloalkyl, cyano, nitro, amino, hydrazido, alkylthio, alkenyl, alkynyl or $R_{1j}$;

(xiii) indol-6-yl substituted at the 5 position by amino, hydroxy, halo (such as fluoro or chloro), alkyl, carboxy, alkoxycarbonyl, cyano, amido, aminoalkyl, alkoxy or alkylthio and optionally substituted at the 3 position by halo (such as chloro), haloalkoxy, haloalkyl, cyano, nitro, amino, hydrazido, alkylthio, alkenyl, alkynyl or $R_{1j}$; or (xiv) benzo[b]thiophen-2-yl optionally substituted at the 3 position by amino, hydroxy, halo, alkyl, carboxy, cyano, amido, aminoalkyl, alkoxy or alkylthio and at the 5 or 6 position by halo, haloalkoxy, haloalkyl, cyano, nitro, amino, hydrazido, alkylthio, alkenyl, alkynyl or $R_{1j}$.

Examples of particular values for substituents that may be present on $R_2$ are:
for halo: fluoro, chloro, bromo or iodo;
nitro;
thiol;
for haloalkoxy: difluoromethoxy or trifluoromethoxy;
hydrazido;
for alkylhydrazido: methylhydrazido;
amino;
cyano;
for haloalkyl: trifluoromethyl;
for alkylthio: methylthio;

for alkenyl: vinyl;
for alkynyl: ethynyl;
for acylamino: acetylamino;
carboxy;
for acyloxy: acetoxy;
hydroxy;
for alkyl: methyl or ethyl;
amido ($CONH_2$);
for aminoalkyl: aminomethyl; and
for alkoxy: methoxy or ethoxy.

Preferably $R_2$ is optionally substituted by 1 or 2 substituents selected from fluoro, chloro, amino, methyl, ethyl and methoxy.

Examples of particular values for $R_1$ are:
hydrogen;
hydroxy;
for alkoxy: methoxy or ethoxy;
for alkyl optionally substituted by hydroxy, alkylamino, alkoxy, oxo, aryl or cycloalkyl: alkyl, such as methyl or ethyl, alkylaminoalkyl, such as dimethylaminomethyl, or alkanoyl, such as acetyl;
for hydroxyalkyl: hydroxymethyl;
for alkoxyalkyl: methoxymethyl;
for alkoxycarbonyl: methoxycarbonyl;
for alkylaminocarbonyl: methylaminocarbonyl;
for alkylamino: methylamino, ethylamino or dimethylamino;
for hydroxyalkyl substituted by hydroxy, alkylamino, alkoxy, oxo, aryl or cycloalkyl: carboxyl or carboxymethyl; and
for aminoalkyl substituted by hydroxy, alkylamino, alkoxy, oxo, aryl or cycloalkyl: amido ($CONH_2$) or amidomethyl.

Examples of particular values for $R_{1j}$ are:
hydrogen;
hydroxy;
for alkoxy: methoxy or ethoxy;
for alkyl optionally substituted by hydroxy, alkylamino, alkoxy, oxo, aryl or cycloalkyl: alkyl, such as methyl or ethyl, or alkanoyl, such as acetyl;
for hydroxyalkyl: hydroxymethyl;
for alkoxyalkyl: methoxymethyl;
for alkoxycarbonyl: methoxycarbonyl;
for alkylamino: methylamino, ethylamino or dimethylamino;
for hydroxyalkyl substituted by hydroxy, alkylamino, alkoxy, oxo, aryl or cycloalkyl: carboxyl or carboxymethyl; and
for aminoalkyl substituted by hydroxy, alkylamino, alkoxy, oxo, aryl or cycloalkyl: amido ($CONH_2$) or amidomethyl.

More preferably $R_2$ represents:
(i) phenyl optionally being substituted in the 3 and/or 4 position by fluoro, chloro, bromo, iodo, nitro, difluoromethoxy, trifluoromethoxy, amino, cyano, trifluoromethyl, methylthio, vinyl, carboxy, acetoxy, $MeSO_2$—, hydroxy, methoxy, ethoxy, methyl, methoxycarbonyl, methylamino, ethylamino or amido, and optionally substituted at the 6 position by amino, hydroxy, fluoro, methoxycarbonyl, cyano or aminomethyl (preferably phenyl substituted in the 4 position by chloro, amino, vinyl, methylamino, methyl or methoxy, optionally at the 3 position with amino or hydroxy, and optionally at the 6 position with amino or hydroxy);
(ii) naphth-2-yl optionally substituted at the 6, position by hydroxy and optionally substituted at the 3 position by amino or hydroxy;
(iii) isoquinolin-7-yl, indol-5-yl, indol-6-yl, indazol-5-yl, indazol-6-yl, benzothiazol-6-yl or benzisoxazol-5-yl optionally substituted at the 3 position by chloro, bromo, amino, methyl or methoxy (preferably indol-6-yl optionally substituted at the 3 position by chloro, bromo, methyl or methoxy);
(iv) benzimidazol-5-yl or benzothiazol-6-yl optionally substituted at the 2 position by amino;
(v) thien-2-yl or thien-3-yl optionally substituted at the 4 or 5 position by methylthio, methyl or acetyl;
(vi) 3,4-methylenedioxyphenyl, 2,3-dihydroindol-6-yl, 3,3-dichloro-2-oxo-indol-6-yl or 1-methyl-3-aminoindazol-5-yl;
(vii) benzothiazol-2-yl, imidazo[1,2-a]pyrimidin-2-yl or tetrahydroimidazo[1,2-a]pyrimidin-2-yl;
(viii) pyrazol-2-yl substituted at the 5 position by methyl;
(ix) pyrid-2-yl optionally substituted at the 6 position by chloro;
(x) pyrid-3-yl optionally substituted at the 4 position by chloro;
(xi) benzofur-2-yl optionally substituted at the 3 position by chloro, methyl or methoxy, at the 5 or 6 position by methyl and at the 6 position by methoxy;
(xii) indol-2-yl optionally substituted on the indole nitrogen atom by methyl and optionally substituted at the 5 or 6 position by fluoro, chloro, bromo, methyl or methoxy;
(xiii) indol-6-yl substituted at the 5 position by chloro, fluoro or hydroxy and optionally substituted at the 3 position by chloro or methyl; or
(xiv) benzo[b]thiophen-2-yl optionally substituted at the 3 position by fluoro, chloro or methyl, and optionally substituted at the 5 or 6 position by fluoro, chloro, methyl, hydroxy, or methoxy.

Examples of particular values for $R_2$ are:
(i) phenyl, 2-aminophenyl, 3-aminophenyl, 2-amino-3-fluorophenyl, 2-amino-4-fluorophenyl, 2-amino-4-chlorophenyl, 2-amino-3-bromophenyl, 2-amino-3-nitrophenyl, 2-amino-4-nitrophenyl, 3,4-dimethoxy-5-aminophenyl, 2-amino-4-methylphenyl, 2-amino-3-methylphenyl, 2-amino-3-methoxyphenyl, 3,4-diaminophenyl, 3,5-diaminophenyl, 3-amino-4-fluorophenyl, 3-amino-4-chlorophenyl, 3-amino-4-bromophenyl, 3-amino-4-hydroxyphenyl, 3-amino-4-carboxymethylphenyl, 3-amino-4-methylphenyl, 3-amino-4-methoxyphenyl, 2-fluorophenyl, 4-fluoro-3-cyanophenyl, 3-chlorophenyl, 3-chloro-4-hydroxphenyl, 3-chloro-5-hydroxyphenyl, 4-chlorophenyl, 4-chloro-2-hydroxyphenyl, 4-chloro-3-hydroxyphenyl, 4-chloro-3-methylphenyl, 4-chloro-3-methoxyphenyl, 4-bromophenyl, 4-bromo-3-methylphenyl, 4-iodophenyl, 2-cyanophenyl, 3-cyanophenyl, 4-cyanophenyl, 3-cyano-5-aminophenyl, 2-hydroxphenyl, 2-hydroxy-4-methoxyphenyl, 3-hydroxphenyl, 3-hydroxy-4-methylphenyl, 2,4-dihydroxyphenyl, 3,4-dihydroxyphenyl, 3-hydroxy-4-methoxyphenyl, 4-difluoromethoxyphenyl, 4-trifluoromethoxphenyl, 4-trifluoromethylphenyl, 4-methylthiophenyl, 4-methoxycarbonylphenyl, 4-acetoxyphenyl, 4-methanesulfonylphenyl, 3-methylphenyl, 3-methyl-5-aminophenyl, 4-methylphenyl, 4-vinylphenyl, 4-methoxyphenyl, 4-ethoxyphenyl, 4-methoxy-3-chlorophenyl, 4-methoxy-3-methylphenyl, 3-methylaminophenyl, 4-methylaminophenyl, 4-ethylaminophenyl or 2-aminomethylphenyl;
(ii) naphth-2-yl, 3-aminonaphth-2-yl, 3-hydroxynaphth-2-yl or 6-hydroxynaphth-2-yl;

(iii) isoquinolin-7-yl, indol-5-yl, indol-6-yl, 3-chloroindol-6-yl, 3-bromoindol-6-yl, 3-methylindol-6-yl, 3-methoxyindol-6-yl, indazol-5-yl, 3-aminoindazol-5-yl, indazol-6-yl, benzothiazol-6-yl, 3-aminobenzisoxazol-5-yl;

(iv) benzimidazol-5-yl, 2-aminobenzimidazol-5-yl, or benzothiazol-6-yl;

(v) thien-2-yl, 5-methylthien-2-yl, 5-methylthio-thien-2-yl, 5-acetylthien-2-yl or thien-3-yl;

(vi) 3,4-methylenedioxyphenyl, 2,3-dihydroindol-6-yl, 3,3-dichloro-2-oxo-indol-6-yl or 1-methyl-3-aminoindazol-5-yl;

(vii) benzothiazol-2-yl, imidazo[1,2-a]pyrimidin-2-yl or tetrahydroimidazo[1,2-a]pyrimidin-2-yl;

(viii) 5-methylpyrazol-2-yl;

(ix) 5-chloropyrid-2-yl;

(x) pyrid-3-yl, 6-chloropyrid-3-yl;

(xi) benzofur-2-yl, 5-chlorobenzofur-2-yl, 3-methylbenzofur-2-yl, 5-methylbenzofur-2-yl, 6-methoxybenzofur-2-yl;

(xii) indol-2-yl, 5-fluoroindol-2-yl, 5-chloroindol-2-yl, 5-methylindol-2-yl, 5-methoxindol-2-yl, 6-methoxyindol-2-yl and 1-methyl-indol-2-yl;

(xiii) 5-fluoroindol-6-yl; or (xiv) benzo[b]thiophen-2-yl, 5-chloro-benzo[b]thiophen-2-yl or 6-chlorobenzo[b]thiophen-2-yl.

$R_2$ may, for example, be selected from one of the formula (A') to (H'):

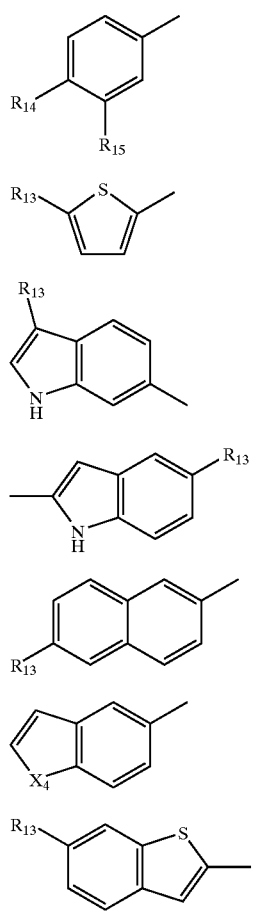

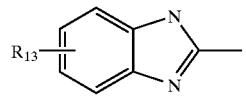

wherein $X_4$ is O or S, $R_{13}$ is selected from hydrogen, chloro or methyl and $R_{14}$ is selected from hydrogen, methyl, ethyl, fluoro, chloro, and methoxy and $R_{15}$ is selected from hydrogen, methyl, fluoro, chloro and amino.

Preferably $R_2$ is of the formula (A') (wherein $R_{14}$ is selected from hydrogen, methyl, ethyl, fluoro, chloro, and methoxy and $R_{15}$ is selected from hydrogen, methyl, fluoro, chloro and amino) or of the formula (B') (wherein $R_{13}$ is chloro) or of the formula (C') (wherein $R_{13}$ is selected from hydrogen, methyl and chloro) or of the formula (D') (wherein $R_{13}$ is selected from hydrogen and chloro) or of the formula (E') (wherein $R_{13}$ is hydrogen) or of the formula (G') (wherein $R_{13}$ is chloro).

More preferably $R_2$ is 4-methoxyphenyl, 5-chloroindol-2-yl, 3-chloroindol-6-yl, indol-6-yl or 3-methylindol-6-yl.

$R_2$ is preferably of the formula (A') and $R_{14}$ and $R_{15}$ are as defined hereinabove. More preferably $R_2$ is of the formula (A') and $R_{14}$ is methoxy and $R_{15}$ is hydrogen.

It is preferred that at least one of $R_6$ and $R_7$ be other than hydrogen and that $R_6$, if present, is preferably a substituent containing one or more polar hydrogens such as hydroxy, amino, alkylamino, alkylaminoalkyl, aminocarbonyl, alkylaminocarbonyl, hydrazo and alkylhydrazo; alternatively $R_6$ and $R_7$ are joined together in the formation of a naphthyl or indolyl or azaindolyl or diazaindolyl group.

It is especially preferred that $R_6$ be amino and $R_7$ be chloro, bromo, methyl, methoxy or vinyl; or that $R_6$ and $R_7$ taken together form an indolyl ring with the NH at the 6-position or taken together form a naphthyl ring.

The compounds of the invention may be prepared by conventional chemical synthetic routes or by routes as illustrated by the following examples.

The compounds of the formula (I) may be prepared by forming the —X—X— bond from appropriate intermediates. For example, when —X—X— is —CONH— or —CO—NR$_{1a}$—, by reacting a compound of the formula (10): H$_2$N—Y—(Cy)—L—Lp(D)$_n$ with a compound of the formula R$_2$—COOH, under conditions known for the formation of an amide bond. The reaction is conveniently carried out in the presence of a benzotriazole-based reagent such as 1-hydroxybenzotriazole or 1-hydroxy-7-azabenzotriazole, in an inert organic solvent such as dimethylformamide and/or methylene chloride. The reaction mixture is usually taken to 0° C. and then a dehydrating agent such as dicyclohexylcarbodiimide or 1-(3-dimethylaminopropyl)-3-ethylcarbodiimide added. Other suitable reagents and solvents are known in the art. For example, an acid of formula R$_2$COOH may be converted into an acid halide, such as an acid chloride, and then reacted with the compound of formula (10) in the presence of a base, such as pyridine. Another reagent is diethyl cyanophosphonate.

Compounds wherein —X—X— is —NHCO— or —NHCH$_2$— may be formed from the appropriate intermediates using reaction conditions for the formation of an amide bond as described above and if necessary subsequent reduction of the resulting amide bond.

Compounds of the formula (I) wherein —X—X— is of the formula —CH$_2$NH— may be prepared by reducing the corresponding compound of the formula (I) wherein —X—X— is —CONH—, or by reaction of a compound of formula (10)

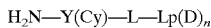

with a compound of the formula $R_2CHO$ and reducing the intermediate of formula (I) where X—X is C=N— with, for example, sodium cyanoborohydride.

When —X—X— is —CH=CH—, the compounds of the formula (I) may be prepared using the Wittig or Horner-Emmons reactions. The corresponding compound in which —X—X— is —CH$_2$CH$_2$— can be formed by reduction of the —CH=CH— group, for example with hydrogen over a palladium-on-carbon catalyst.

An —X—X— bond of the formula —COO— or —OC(O)— may be formed by reacting the appropriate hydroxy and activated carboxylic acid (e.g. acid chloride or reactive ester) intermediates under conditions known for ester bond formation. Alternatively, a hydroxy and a carboxylic acid intermediate could be reacted together in the presence of diethylazodicarboxylate/triphenylphosphine.

An —X—X— bond of the formula —CH$_2$O— or —OCH$_2$— may be formed by reacting the appropriate hydroxy intermediate with the appropriate alkyl halide in the presence of a base. Conditions for the formation of an ether bond are known in the art.

These reactions can also be used to form intermediates, which contain one of the above —X—X— bonds.

Compounds of the formula (I) may also be prepared by introducing the Lp(D)n group into a compound of the formula (11):

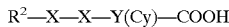

Reactive groups in Lp(D)$_n$ which could cause side-reactions can of course be protected. The reaction between the compound (11) and H—Lp(D)$_n$ is conveniently carried out in an inert organic solvent, in the presence of an organic base such as an amine (e.g. ethyldiisopropylamine), additionally in the presence of a reagent such as diethylcyanophosphonate.

Intermediates which already contain the Lp(D)$_n$ group may be prepared from the appropriate carboxy compound using similar reaction conditions to those described above.

Compounds of the formula (I) can also be prepared by reacting a compound of the formula (12):

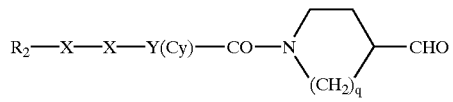

or (13):

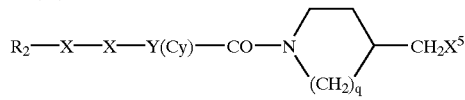

(wherein $X^5$ is a leaving group such as tosyloxy, mesyloxy or halo) with a compound of formula $HNR_aR_b$. The reaction between the compound of formula (12) and $HNR_aR_b$ may be carried out in the presence of a reducing agent, such as sodium cyanoborohydride, for example using conditions similar to those described in Examples 1 to 5. The reaction between the compound of formula (13) and $HNR_aR_b$ may be carried out in an inert organic solvent such as THF, in the presence of an inorganic base such as potassium carbonate, and preferably in the presence of sodium iodide. The reaction usually takes place at or near reflux of THF.

Intermediates containing the Lp(D)$_n$ group can also be formed using these reactions from appropriate intermediates, although normally the introduction of the $HNR_aR_b$ group is the last step in the synthesis.

Hence the present invention also provides a process for the preparation of a compound of formula (I) comprising:
a) when —X—X is —CONH—, reacting a compound of formula (10) with a compound of formula $R_2$—COOH, under amide bond-forming conditions;
b) reacting a compound of formula (11) with a compound of formula H—Lp(D)$_n$ under amide bond-forming conditions; or
c) reacting a compound of formula (12) or (13) with a compound of formula $HNR_aR_b$;
wherein $R_2$, $R_a$, $R_b$ and Lp(D)$_n$ are as hereinabove defined and formulae (10), (11), (12) and (13) are as hereinabove defined.

A compound of the formula (12) or (13) may be formed from the corresponding hydroxymethyl compound of formula (14).

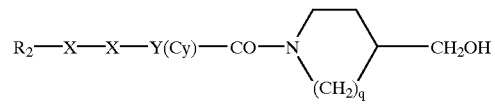

Oxidation of the hydroxymethyl compound with a suitable mild oxidising agent for the formation of aldehydes, such as N-methylmorpholine oxide in the presence of tetrapropylammonium perruthonate, can be used to form a compound of the formula (12).

Other possible oxidising agents include manganese dioxide or DMSO/oxalyl chloride or DMSO/SO$_3$ or Dess-Martin reagent.

A compound of formula (13) can be formed from the hydroxymethyl compound of formula (14) by introducing the leaving group X. When X is mesyloxy or tosyloxy, the hydroxymethyl compound may be reacted with the mesyl or tosyl halide in the presence of an organic base, such as triethylamine, in an inert organic solvent such as dichloromethane.

A hydroxymethyl compound of formula (14) in which X—X is CONH may be prepared by reacting a compound of formula (15).

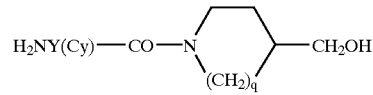

with a compound of formula $R_2COOH$ under amide bond forming conditions, as described previously.

A compound of formula (15) may be prepared by reacting a compound of formula (16).

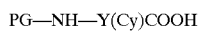

in which PG is an amino protecting group, such as t-butoxycarbonyl, with a compound of formula (17)

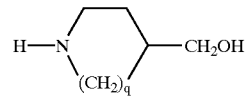

under amide bond forming conditions, to afford a compound of formula (18)

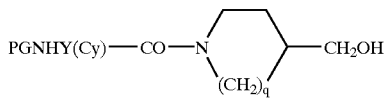

followed by removal of the protecting group, PG.

A compound of formula (10) may be prepared by reacting a compound of formula (16) with a compound of formula H—Lp(D)$_n$ under amide bond-forming conditions to afford a compound of formula (19), followed by removing the protecting group PG.

A compound of formula (11) in which X—X is CONH may be prepared by reacting a compound of formula (20)

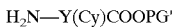

in which PG' represents a carboxyl protecting group with a compound of formula $R_2$COOH under amide bond-forming conditions to afford a compound of formula (21)

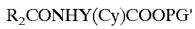

followed by removing the protecting group PG'.

When —X—X is —CONH— and Y is CH, a compound of formula (I) may be prepared by a number of steps from an amino acid derivative using the reactions described above. For example, see Scheme I.

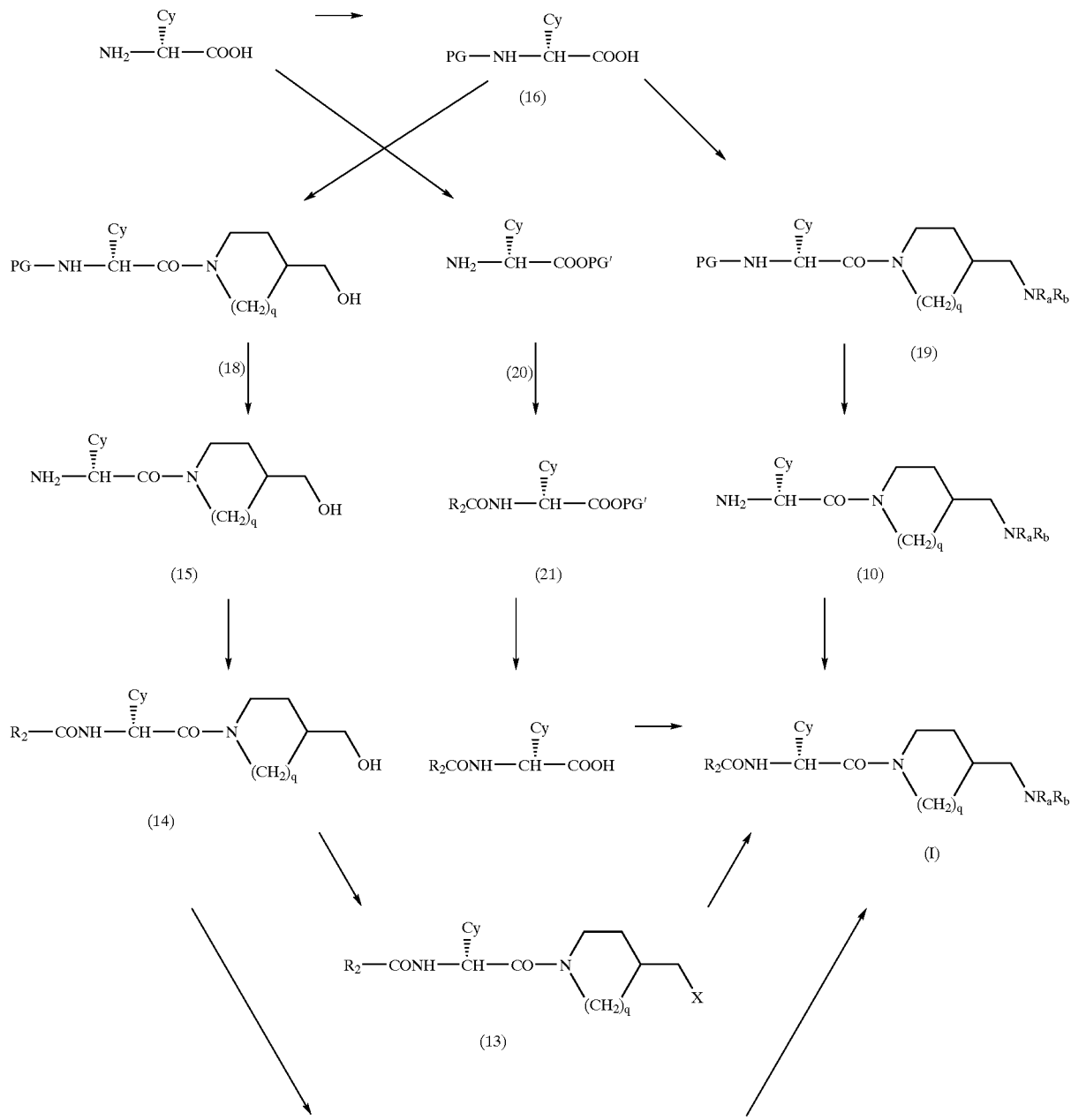

Scheme 1

-continued

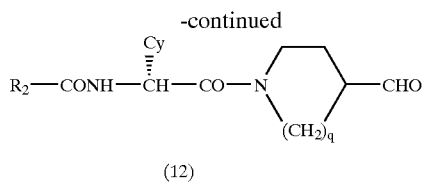

(12)

PG is an amino-protecting group
PG' is a carboxy-protecting group

An amino acid from Scheme I may be prepared (for example) by one or more of the following methods:

(i) from aryl or heteroaryl aldehydes via the Strecker synthesis or modifications thereof, via Bucherer-Bergs hydantoin synthesis, or via the Ugi methodology ("Isonitrile Chemistry", Ugi I. Ed.; Academic: New York, 1971;145–1999, "Multicomponent Reactions with Isocyanides", Domling, A.; Ugi, I. *Angew. Chem. Int. Ed.* 2000, 39, 3168; "Amino Acid Derivatives by Multicomponent Reactions", Dyker, G. *Angew, Chem. Int. Ed. Engl.* 1997, 36, 1700; and also see "A new Class of Convertible Isocyanides in the Ugi Four-Component Reaction", Lindhorst, T.; Bock H.; Ugi, I. *Tetrahedron*, 1999, 55, 7411.) with removal and replacement of protecting groups;

(ii) from styrenes via Sharpless methodology (J. Am. Chem. Soc. 1998, 120, 1207–1217)

(iii) from aryl boronic acids via Petasis methodology (Tetrahedron, 1997, 53, 16463–16470) with removal and replacement of protecting groups;

(iv) from aryl and heteroaryl acetic acids—via Evan's azidation (Synthesis, 1997, 536–540) or by oximation, followed by reduction and addition of protecting groups; or (v) from existing aryl glycines by manipulation of functional groups, for example, alkylation of hydroxy groups, palladium assisted carbonylation of triflates derived from hydroxy groups and further manipulation of the carboxylic esters to give carboxylic acids by hydrolysis, carboxamides by activation of the carboxylic acid and coupling with amines, amines via Curtius reaction on the carboxylic acid, or alkylsulphonyl compounds by oxidation of alkylthio compounds;

(vi) from aliphatic, carbocylic and non-aromatic heterocyclic aldehydes and ketones using a Horner-Emmons reaction with N-benzyloxycarbonyl)-α-phosphonoglycine trimethyl ester (Synthesis, 1992, 487–490), or by any other method known in the art or (vii) from oximes of formula

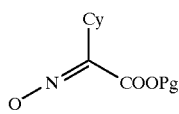

in which Pg is a carboxy protecting group, by reduction.

A starting material for the preparation of a compound of formula (I), where the alpha atom is nitrogen, may be produced, for example, by reaction of a beta protected hydrazine (such protection to be chosen as to be compatible with the subsequent reagents to be employed) with phosgene, diphosgene, triphosgene or N,N'carbonyl diimidazole to give a reactive compound of the type PGNHN(Cy)COCl or PGNHN(Cy)CO-imidazole (wherein PG is a protecting group).

This intermediate may be used as has been described above for the carboxylic starting reagents where the alpha atom is carbon.

The skilled person will be aware that at certain stages in the synthesis of a compound of formula (I) it may be necessary to protect a reactive functional group in the molecule to prevent unwanted side-reactions.

The protection of amino and carboxylic acid groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include $C_1$–$C_6$ alkyl groups such as methyl, ethyl, t-butyl and t-amyl; aryl ($C_1$–$C_4$)alkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl.

Examples of amine protecting groups (PG) include acyl groups, such as groups of formula RCO in which R represents $C_{1-6}$ alkyl, $C_{3-10}$ cycloalkyl, phenyl $C_{1-6}$ alkyl, phenyl, $C_{1-6}$ alkoxy, phenyl $C_{1-6}$ alkoxy, or a $C_{3-10}$ cycloalkoxy, wherein a phenyl group may be optionally substituted, for example by one or two of halogen, $C_1$–$C_4$ alkyl and $C_1$–$C_4$ alkoxy.

Preferred amino protecting groups include benzyloxycarbonyl (CBz), t-butoxycarbonyl (Boc) and benzyl.

In another aspect the invention relates to a process for preparing a compound of formula I comprising deprotecting a compound of formula (I'):

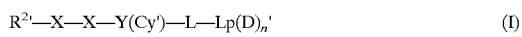

wherein $R^{2'}$ is $R^2$ (as hereinabove defined) or protected $R^2$, Cy' is Cy (as hereinabove defined) or protected Cy and $Lp(D)_n'$ is $Lp(D)_n$ (as hereinabove defined) or protected $Lp(D)_n$; providing at least one protecting group is present.

If necessary physiologically tolerable salts can be formed using methods known in the art.

It will be understood that the compounds of formula (I) may be isolated in the form of salts or solvates (which may or may not be physiologically tolerable), and that all such salts and solvates are therefore included within the scope of the present invention.

All novel intermediates described herein are provided as further aspects of the invention.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. Preferably the compositions will be sterile and in a solution or suspension form suitable for injection or infusion. Such compositions form a further aspect of the invention.

The following are examples of pharmaceutical compositions of compounds according to the invention.

Formulation 1

Hard Gelatin Capsules are Prepared Using the Following Ingredients

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

Tablets Each Containing 60 mg of Active Ingredient are Made as Follows

|  |  |
| --- | --- |
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Viewed from this aspect the invention provides a pharmaceutical composition comprising a serine protease inhibitor according to the invention together with at least one pharmaceutically acceptable carrier or excipient. The pharmaceutical composition may also optionally comprise at least one further antithrombotic and/or thrombolytic agent.

Viewed from a further aspect the invention provides the use of a serine protease inhibitor according to the invention for the manufacture of a medicament for use in a method of treatment of the human or non-human animal body (e.g. a mammalian, avian or reptilian body) to combat (i.e. treat or prevent) a condition responsive to said inhibitor.

Viewed from a further aspect the invention provides a method of treatment of the human or non-human animal body (e.g. a mammalian, avian or reptilian body) to combat a condition responsive to a serine protease inhibitor (e.g. a condition such as a thrombotic disorder responsive to a factor Xa inhibitor), said method comprising administering to said body an effective amount of a serine protease inhibitor according to the invention.

The dosage of the inhibitor compound of the invention will depend upon the nature and severity of the condition being treated, the administration route and the size and species of the patient. However in general, quantities of from 0.01 to 100 μmol/kg bodyweight will be administered.

All publications referred to herein are hereby incorporated by reference.

The invention will now be described further with reference to the following non-limiting Examples.

Experimental

Abbreviations used follow IUPAC-IUB nomenclature. Additional abbreviations are HPLC, high-performance liquid chromatography; rpHPLC, reverse phase HPLC; SCX, strong cation exchange resin; THF, tetrahydrofuran; HOAc, acetic acid; DMSO, dimethyl sulfoxide (perdeuterated if for NMR); EtOAc, ethyl acetate; EtOH, ethanol; DMF, dimethylformamide; DCM, dichloromethane; HOAT, 1-hydroxy-7-azabenzotriazole; HOBT, 1-hydroxy benzotriazole; EDCI, 1-(3-Dimethylaminopropyl)-3-ethylcarbodiimide hydrochloride; DIPEA, diisopropylethylamine; Boc, tertiary butyloxycarbonyl; TEA, triethylamine; TFA, trifluoroacetic acid; MALDI-TOF, Matrix assisted laser desorption ionisation-time of flight mass spectrometry, CI-MS, chemical ionization mass spectrum; API-MS (atmospheric pressure chemical ionization mass spectra) were obtained on a PESciex (trademark) API 150EX with a heated nebulizer and nitrogen as the reagent gas in positive ion mode. RT, retention time; TLC, thin layer chromatography with $R_f$ as relative mobility. All solution concentrations are expressed as % Vol./% Vol. unless otherwise stated. Reagents were obtained from a variety of commercial sources.

IR means an infrared spectrum was obtained. $^1$NMR, 1H-NMR, or 1H NMR means a proton magnetic resonance spectrum was obtained.

In general in this specification, "D—" or "R—" in the name of a product indicates the product was made beginning with a chiral starting material, for example D-phenylglycine; however, racemization may have occurred, and the enantiomeric purity may not have been determined.

General Experimental Procedures

Purification of Compounds (rpHPLC Chromatography)

Material is or was purified using standard reverse-phase preparative chromatography techniques. A 5 micron, 20×50 mm O.D. C18 column is or was used (YMC ODS-A) with a flow rate of 20 mL/min and an standard elution time of 10–15 minutes. A gradient of water:acetonitrile (between 95:5 to 5:95; each eluent w/0.1% TFA) over the elution time is or was used. Fractions containing product are or were concentrated, frozen, and lyophilized to afford, when applicable, the trifluoroacetate salt of the product. The free base can or could be obtained, if desired, by loading a methanolic solution of the trifluoroacetate salt onto an ion-exchange resin (SCX, Varian) and subsequent elution of the resin with methanol followed by 2 N ammonia in methanol. Concentration of the later fractions affords or afforded the free base product. Preparation of a hydrochloride salt from the free base is or was completed by treatment an organic solution of the free base (EtOAC, methylene chloride) with anhydrous HCl in diethyl ether and concentration.

Preparation of Starting Materials and Intermediates

Intermediate substituted glycine compounds for starting materials and intermediates, including those in which the amino group and/or the carboxy group is protected, conveniently may be prepared using one of the procedures below, or by a similar procedure. It may be convenient or preferred to change the order of steps in the preparation of a compound of the invention and to use a similar procedure with a different intermediate. In particular, it may be convenient to use an acyl group $R_2$—CO— initially in a preparation, rather than an amino protecting group.

Abbreviations, in addition to others listed herein, include: TEMPO: 2,2,6,6-tetramethyl-1-piperidinyloxy, free radical; (DHQD)$_2$PHAL: hydroquinidine 1,4-phthalazinediyl diether; r.b. or rb, round bottomed; PPh$_3$, triphenylphosphine; Boc$_2$O or Boc anhydride: di-tert-butyl dicarbonate.

Preparation of Intermediates KE-1-KE-5

The following compounds were prepared according to the indicated method (Method KE-A) from the indicated starting materials, unless otherwise described.

Intermediate KE-1

Ethyl oxo-quinolin-8-ylacetate

Method KE-A

To a stirring solution of 8-bromoquinoline (10.1 g, 48.5 mmol) in THF (500 mL) at −78° C. was added dropwise a 1.3 M solution of sec-butyl lithium (37.3 mL, 48.5 mmol) in cyclohexane. After 5 min, diethyl oxalate (8 mL, 58.3 mmol) was added; and the solution was allowed to slowly warm to room temperature overnight. The next morning, the reaction was quenched with the addition of saturated aqueous NH$_4$Cl; and the solvent was removed in vacuo. The residue was partitioned between ethyl acetate and satd aq. NaHCO$_3$; the layers were separated; and then the aqueous phase was washed with brine, dried with MgSO$_4$, filtered and concentrated in vacuo. The residue was chromatographed over silica gel, eluting with 20% ethyl acetate/hexanes through 25% ethyl acetate/hexanes. The product containing fractions were combined and concentrated in vacuo to give 5.88 g (53%) of the title compound.

1H-NMR

IS-MS, m/e 230.1 (M+1)

Intermediate KE-2

Ethyl oxo-quinolin-5-ylacetate

Prepared from 5-bromoquinoline and diethyl oxalate using Method KE-A.

1H-NMR

IS-MS, m/e 230.0 (M+1)

Intermediate KE-3

Ethyl oxo-thiazol-5-ylacetate

To a r.b. flask (500 cm$^3$) under argon, fitted with ethanol thermometer, septum cap, and dropping funnel, was added anhydrous ether (100 cm$^3$) with stirring. This was cooled to −78° C. and 2 M n-butyllithium (60 cm$^3$, 120 mmol) was added.

A solution of silyl thiazole (16 g, 16 cm$^3$, 100 mmol) in anhydrous ether (100 cm$^3$) was then added by dropping funnel over 30 minutes. This was allowed to stir for 1 hour to give a peach suspension. To this was added diethyl oxalate (16.3 cm$^3$, 17.5 g, 120 mmol) rapidly to give a brown solution, resulting in a temperature increase to −30° C. This was allowed to cool back to −78° C. and stirred for 30 minutes. Reaction monitored by $^1$H NMR (CDCl$_3$).

The brown solution was poured onto 5% hydrochloric acid solution (300 cm$^3$) with vigorous stirring for 30 minutes. Ether layer was separated and washed with saturated bicarbonate (ca. 80 cm$^3$), dried over magnesium sulphate, and concentrated in vacuo to give an orange oil. This was purified by flash chromatography (10% ethyl acetate/hexane) to give a yellow oil (7.31 g, 39.47 mmol) [40% Yield].

$^1$H NMR (CDCl$_3$); 1.42 (3H, t), 4.45 (2H, q), 8.89 (1H, s), 9.10 (1H, s).

Intermediate KE-4

Ethyl oxo-thiazol-2-ylacetate

Prepared from thiazole and diethyl oxalate using Method KE-A. In this case the temperature was held at −35° C. and n-butyllithium in hexane was used in place of sec-butyllithium in cyclohexane.

$^1$NMR

IS-MS, m/e 165.0 (M+1)

Intermediate KE-5

Ethyl oxo-isoquinolin-8-ylacetate

Prepared from 8-bromoisoquinoline and diethyl oxalate using Method KE-A, substituting n-butyl lithium in hexanes for sec-butyl lithium in cyclohexane.

1NMR

IS-MS, m/e 230.0 (M+1)

Analysis for $C_{13}H_{11}NO_3$:

Calcd: C, 68.11; H, 4.84; N, 6.11;

Found: C, 68.11; H, 5.00; N, 6.14.

Preparation of Intermediates OX-1–OX-9

The following compounds were prepared according to the indicated method (Method OX-A or Method OX-B) from the indicated starting materials unless otherwise described.

Intermediate OX-1

Ethyl Hydroxyimino-pyridin-2-ylacetate

Method OX-A

To a stirring solution of ethyl 2-pyridylacetate (12.6 g, 76.3 mmol) in acetic acid (19 mL) at 5° C. was added a solution of sodium nitrite (6.05 g, 87.7 mmol) in water (12 mL) at a rate sufficient to maintain the internal temperature below 15° C. After complete addition and an additional 30 min, an additional 30 mL of water were added. The resulting white precipitate was filtered, washed with water, satd aq. NaHCO$_3$, and again with water. The solid was then dried under vacuum to give 14.1 g (95%) of the title compound.

1H-NMR

IS-MS, m/e 194.9 (M+1)

Analysis for $C_9H_{10}N_2O_3$:

Calcd: C, 55.67; H, 5.19; N, 14.43;

Found: C, 55.79; H, 5.14; N, 14.13.

Intermediate OX-2

Ethyl Hydroxyimino-pyridin-3-ylacetate

Using the procedure of Tikk et al [Acta. Chimica, Hungarica, 114(3–4), 355], a mixture of ethyl hydroxyimino-pyridin-3-yl-acetate and n-butyl hydroxyimino-pyridin-3-yl-acetate was prepared from ethyl 3-pyridinylacetate and n-butyl nitrite.

1H-NMR

IS-MS, m/e 195 (M+1), 223.1 (M+1)

Intermediate OX-3

Ethyl Hydroxyimino-quinolin-8-ylacetate

Method OX-B

To a stirring solution of ethyl oxo-quinolin-8-yl-acetate (5.5 g, 24 mmol) in ethanol (140 mL) was added sodium acetate (2.16 g, 26.4 mmol) followed by hydroxylamine hydrochloride (2.67 g, 38.4 mmol). The mixture was heated to reflux; and, after 7 h, the heating mantle was removed and the solution was allowed to stir overnight at room temperature. The next morning, the solvent was removed in vacuo and the residue was partitioned between ethyl acetate and satd aq. NaHCO$_3$. The layers were separated and the organic phase was washed with brine, dried with Na$_2$SO$_4$, filtered and concentrated in vacuo. The resulting foam was recrystalized from dichloromethane/hexanes to give an initial crop of 2.5 g of the title compound as an off-white solid, followed by 0.31 g of a second crop. The mother liquor was then concentrated in vacuo, the residue was dissolved in a minimal amount of dichloromethane. The solution was then chromatographed over silica gel, eluting with 30% ethyl acetate/hexanes, then 40% ethyl acetate/hexanes, and finally with ethyl acetate. The product containing fractions were combined and concentrated in vacuo to give 1.94 g of the title compound for a combined yield of 4.75 g (81%).

1H-NMR
IS-MS, m/e 245.0 (M+1)
Intermediate OX-4
Ethyl Hydroxyimino-quinolin-5-ylacetate Prepared from ethyl oxo-quinolin-5-yl-acetate using Method OX-B.

1H-NMR
IS-MS, m/e 245.0 (M+1)
Intermediate OX-5
Ethyl Hydroxyimino-thiazol-5-ylacetate To a r.b. flask (500 cm$^3$) was added the ethyl oxo-thiazol-5-ylacetate (6.30 g, 34.02 mmol) to ethanol (ca. 180 cm$^3$) with stirring. Sodium acetate (3.06 g, 37.30 mmol) and hydroxylamine hydrochloride (3.78 g, 54.43 mmol) were then added to give an off-white suspension. This was brought to reflux at 85° C. for 1 hour. Reaction monitored by TLC (60% hexane/ethyl acetate; s.m. r.f 0.5, prod. r.f. 0.3.). Reaction cooled and concentrated in vacuo. Product taken up in ethyl acetate (c.a. 200 cm$^3$) and washed with 5% hydrochloric acid solution. Ethyl acetate layer was dried over magnesium sulphate and evaporated to dryness to give a cream solid (6.372 g, 31.825 mmol) [94% Yield].

$^1$H NMR (CDCl$_3$); 1.40 (3H, m), 4.40 (2H, m), 8.06 (⅓H, s), 8.78 (⅓H, s), 8.95 (⅔H, s), 8.98 (⅔H, s).
Intermediate OX-6
Ethyl α-Oximino-thiazole-4-acetate To a 2 necked r.b. flask (100 cm$^3$) with ethanol thermometer, concentrated sulphuric acid (25 cm$^3$) was added and cooled to 0° C. with stirring. To this solution was added the ethyl α-oximino-2-aminothiazole-4-acetate (5.00 g, 23.231 mmol). Water (10 cm$^3$) was then added and cooled to −10° C. A solution of sodium nitrite (1.683 g, 24.393 mmol) in water (5 cm$^3$) was then added slowly over an hour keeping the temperature below −5° C.

To a separate r.b. flask (500 cm$^3$), water (180 cm$^3$) was added and cooled to 3° C. The reaction solution was poured in to the cold water with stirring and then cooled to −5° C. To this solution, 50% hypophosphoric acid (90 cm$^3$) was added dropwise over 10 minutes keeping the temperature at −5° C. The solution was allowed to warm to room temperature and stirred overnight. The product was extracted with diethyl ether (ca. 3×150 cm$^3$) and washed with water. The ether layer was concentrated in vacuo and treated to flash chromatography (50% ethyl acetate/n-hexane) to yield a orange oil upon concentration in vacuo (0.60 g, 3.00 mmol) [13% yield].

$^1$H NMR (CDCl$_3$) 1.35 (3H, m), 4.35 (2H, m), 8.4 (1H, s), 8.9 (1H, s), 14.4 (1H, s).
Intermediate OX-7
Ethyl α-Oximino-2-methylthiazole-4-acetate This was prepared from ethyl-γ-chloro-α-oximino-acetoacetate (1.44 g) using the method of Hatanaka et al. (*Journal of Medicinal Chemistry*, 1973, 16(9), 978–984) to yield the titled compound (0.64 g).

$^1$H NMR (CDCl$_3$) 1.35 (3H, t), 2.7 (3H, s), 4.35 (2H, q), 8.2 (1H, s).

Ethyl γ-Chloro-α-oximinoacetoacetate

This was prepared from ethyl oximinoacetoacetate (1.73 g) using the method of Hatanaka et al. (*Journal of Medicinal Chemistry*, 1973, 16(9), 978–984) to yield the titled compound (1.44 g).

$^1$H NMR (CDCl$_3$) 1.25 (3H, t), 4.3 (2H, q), 4.55 (2H, s), 9.45 (1H, s), contains 20% starting material by NMR.
Ethyl Oximinoacetoacetate This was prepared from ethyl acetoacetate (10.00 g) using the method of Fischer (*Organic Synthesis Coll. Vol. 3*, 513–516) to yield the titled compound (12.45 g).

$^1$H NMR (CDCl$_3$) 1.25 (3H, t), 2.35 (3H, s), 4.3 (2H, q), 8.8 (1H, br.).
Intermediate OX-8
Ethyl hydroxyimino-thiazol-2-ylacetate Prepared from ethyl oxo-thiazol-2-ylacetate using Method OX-B.

$^1$NMR
IS-MS, m/e 198.9 (M−1)
Intermediate OX-9
Ethyl hydroxyimino-isoquinolin-8-ylacetate Prepared from ethyl oxo-isoquinolin-8-ylacetate using Method OX-B.

$^1$NMR
IS-MS, m/e 245.0(M+1)
Analysis for $C_{13}H_{12}N_2O_3$:
Calcd: C, 63.93; H, 4.95; N, 11.47;
Found: C, 63.68; H, 4.60; N, 11.34.
Preparation of Intermediates AL-1–AL-3

The following compounds were prepared according to the indicated method (Method AL-A or Method AL-B) from the indicated starting materials, unless otherwise described.
Intermediate AL-1
R-3-Bromo-(1-t-butoxycarbonylamino-2-hydroxyethyl) benzene Method AL-A Sodium hydroxide (3.33 g, 83.25 mmol) was dissolved in water (220 mL), and 20 mL of the resulting solution was removed and added to potassium osmate (410 mg, 1.11 mmol). The remaining sodium hydroxide solution (200 mL) was added to a stirred solution of t-butyl carbamate (9.9 g, 84.5 mmol) in n-propanol (110 mL) followed by freshly prepared t-butyl hypochlorite (9.65 mL; 83.5 mmol). After stirring for 5 min, the solution was cooled to 0° C. A solution of (DHQD)$_2$PHAL (1.30 g, 1.67 mmol) in n-propanol (110 mL) was added, followed by a solution of 3-bromostyrene (5 g, 27.31 mmol) in n-propanol (220 mL), followed by dropwise addition of the potassium osmate/sodium hydroxide solution. The reaction was stirred overnight. Saturated aqueous sodium sulfite (150 mL) was added, and the reaction was stirred for 15 min. The aqueous layer was separated and extracted with ethyl acetate (3×200 mL). The combined organic layers were washed with brine and dried over MgSO$_4$. Removal of solvent under vacuum gave the crude product which was purified by chromatography (silica, 3:2 hexane:ethyl acetate then rechromatographed loading with toluene, gradient elution with hexane—4:1 hexane:ethyl acetate) to give the title product (4.18 g, 49%).

Melting Point=90–91° C.
$^1$H NMR (CDCl$_3$).
Intermediate AL-2
R-3-Methoxycarbonyl-(1-t-butoxycarbonylamino-2-hydroxy-ethyl) benzene Method AL-B In a glass liner containing a stirrer bar was placed Pd(OAc)$_2$ (871 mg, 3.88 mmol), PPh$_3$ (1.96 g, 7.47 mmol, NaOAc (1.48 g, 18.04 mmol) and DMF (82 mL). To this stirred solution was added a solution of R-3-bromo-(1-t-butoxy-carbonylamino-2-hydroxyethyl)benzene (4.27 g, 13.5 mmol) in MeOH (82 mL). The resulting solution was purged with nitrogen and placed in a stirred pressure vessel. The system was charged to 4.1 bar (60 psig) of CO and heated at 95° C. for 36 h. The mixture was cooled to room temperature, filtered through diatomaceous earth, and partitioned between ethyl acetate and water. The organic layer was washed with water (3×) and brine (1×) and dried over $MgSO_4$. Removal of solvent under vacuum gave the crude product which was purified by chromatography (silica gel, gradient elution with 30–35% ethyl acetate/hexane) to provide the title product (3.53 g, 89%).

Melting Point=73–75° C. with decomposition $^1H$ NMR ($CDCl_3$).

API-MS, m/e=240 (M–$C_4H_9$+1).

Intermediate AL-3

R-3-Cyano-(1-t-butoxycarbonylamino-2-hydroxyethyl) benzene

Prepared from 3-cyanostyrene using Method AL-A. 3-Cyanostyrene was prepared using the method described below.

Melting Point=76° C.

$^1H$ NMR ($CDCl_3$).

Preparation of 3-Cyanostyrene

To a stirred suspension of methyltriphenylphosphonium bromide (75 g, 209.71 mmol) in dry THF (750 mL) at 0° C. under nitrogen was added dropwise n-BuLi (83 mL, 2.5 M in hexanes, 207.50 mmol). The mixture was warmed to room temperature. 3-Cyanobenzaldehyde (25 g, 190.65 mmol) was added as a solid in 5 g batches, and the mixture was stirred at room temperature overnight. The reaction was quenched in water, and the solvent was removed under vacuum. The residue was dissolved in the minimal amount of THF, and triphenylphosphine oxide was precipitated using ether. The solid was filtered through diatomaceous earth, and the filtrate was concentrated. Distillation by Kugelrhor at 90° C./33 Pa (0.25 mm Hg) gave the product as a colorless oil (15.5 g, 62%).

Boiling Point=90° C. at 0.25 mmHg.

$^1H$ NMR ($CDCl_3$).

Preparation of Intermediates PAE-1–PAE-18

The following compounds were prepared according to the indicated method (Method PAE-A, Method PAE-B, Method PAE-C, Method PAE-D or PAE-E) from the indicated starting materials, unless otherwise described.

Intermediate PAE-1

Boc-D,L-(2-pyridinyl)glycine Ethyl Ester

Method PAE-A

To a solution of ethyl hydroxyimino-pyridin-2-yl-acetate (7.8 g, 40.15 g) in ethanol (175 mL) and glacial acetic acid (20 mL) was added 5% Pd/C, and the mixture was shaken in a hydrogenation apparatus under an atmosphere of hydrogen at 4.1 bar (45 psig) for 4 h. The mixture was filtered through diatomaceous earth and concentrated in vacuo. The residue was dissolved in THF/$H_2O$ (1/1, 240 mL) and treated with di-tert-butyl dicarbonate (14.23 g, 65.2 mmol) and sodium bicarbonate (27.4 g, 326 mmol). After stirring at room temperature for 2 h, the solution was concentrated in vacuo and the residue was partitioned between EtOAc and water. The organic phase was washed with brine, dried over magnesium sulfate, filtered and concentrated in vacua. The crude material was purified via chromatography over silica gel, eluting with a stepwise gradient of 10–20% ethyl acetate in dichloromethane to give 8.11 g (72%) of the title compound as a yellow oil.

1H-NMR

IS-MS, m/e 281.1 (M+1)

Intermediate PAE-2

Boc-D,L-(3-pyridinyl)glycine Ethyl Ester

Prepared from ethyl hydroxyimino-pyridin-3-ylacetate using Method PAE-A.

1H-NMR

IS-MS, m/e 281.1 (M+1)

Intermediate PAE-3

Boc-D,L-(8-quinolinyl)glycine Ethyl Ester

Method PAE-B

To a stirring solution of ethyl hydroxyimino-quinolin-8-ylacetate (2.4 g, 9.8 mmol) in 50% aq. formic acid (50 mL) at 0° C. was added zinc dust (2 g, 31 mmol). After 1 min, the mixture was filtered through diatomaceous earth and the filtrate was loaded onto an SCX column. After washing the column with methanol, the product was eluted with a 3 to 1 mixture of dichloromethane and (2 N $NH_3$ in methanol). The product containing fractions were combined and concentrated in vacuo to give 2.24 g of light orange oil (IS-MS, m/e 231.0 (M+1)).

The oil (2.14 g, 9.3 mmol) was dissolved in THF (40 mL) and to this stirring solution was added triethylamine (1.4 mL, 10.2 mmol), followed by di-tert-butyl dicarbonate (2.1 g, 9.8 mmol). After 45 min, the solvent was removed in vacuo and the residue was partitioned between ethyl acetate and water. The organic phase was then washed with satd aq. $NaHCO_3$, dried with $Na_2SO_4$, filtered and concentrated in vacuo. The residue was dissolved in a minimum volume of dichloromethane and chromatographed over silica gel, eluting with 5% ethyl acetate in hexanes. The product containing fractions were combined and concentrated to give 2.5 g (81%) of the title compound.

1H-NMR

IS-MS, m/e 331.0 (M+1)

Intermediate PAE-4

Boc-D,L-(5-quinolinyl)glycine Ethyl Ester

Prepared from ethyl hydroxyimino-quinolin-5-ylacetate using Method PAE-B.

1H-NMR

IS-MS, m/e 331.0 (M+1)

Intermediate PAE-5

N-4-Methoxybenzoyl-N-2,4-dimethoxybenzyl-D,L-(2-trifluoro-methylphenyl)glycine Methyl Ester Method PAE-C To 2-trifluoromethylbenzaldehyde (1 g, 5.7 mmol) with stirring was added 2,4-dimethoxybenzylamine (0.86 mL, 5.7 mmol) and methanol (2 mL). After 5 min, the solution was diluted with toluene 100 mL and concentrated in vacuo (twice). The residue was then dissolved in anhydrous methanol (12 mL) and 1,1-dimethyl-2-(methoxycarbonyloxy) ethyl isonitrile [Tetrahedron, 55 (1999) 7411–7420] (0.9 g, 5.7 mmol) was added, followed by 4-methoxybenzoic acid (0.87 g, 5.7 mmol). After stirring for 72 h, the solvent was removed in vacuo and the residue was chromatographed over silica gel, eluting with a step gradient of 30% ethyl acetate in hexanes through 50% ethyl acetate in hexanes. The product containing fractions were combined and concentrated in vacuo; and then the residue was dissolved in ethyl acetate, washed with satd aq. $NaHCO_3$, dried with $Na_2SO_4$, filtered and concentrated to give 1.76 g (48%) of thick oil (NMR, IS-MS, m/e 633.0 (M+1)). The oil (0.5 g, 0.79 mmol) was then dissolved in toluene (5 mL) and concentrated in vacuo (twice) to give a white foam. The residue was then dissolved in THF (3 mL) and potassium tert-butoxide (0.11 g, 0.95 mmol) was added. After 15 min, 12 N HCl (0.079 mL, 0.95 mmol) was added and the solution was allowed to stand overnight in the refrigerator. The next morning, the solvent was removed and the residue was chromatographed over silica gel, eluting with 30% ethyl acetate in hexanes. The product containing fractions were combined and concentrated to give 0.32 g (79%) of the title compound.

1H-NMR

IS-MS, m/e 518.0 (M+1)

Intermediate PAE-6

BOC-D,L-(5-thiazolyl)glycine ethyl ester

To a r.b. flask (250 cm$^3$), D,L-(5-thiazolyl)glycine ethyl ester (4.60 g, 24.7 mmol) was added to tetrahydrofuran (c.a. 100 cm$^3$) with stirring to give a yellow solution. BOC anhydride (5.439 g, 24.948 mmol) and triethyl amine (3.79 cm$^3$, 2.75 g, 27.17 mmol) were then added with stirring for 1 hour. Reaction monitored by TLC (60% hexane/ethyl acetate; s.m. r.f 0.05, prod. r.f. 0.5.). The reaction concentrated in vacuo and product taken up in ethyl acetate (c.a. 150 cm$^3$), washed with 5% hydrochloric acid solution (c.a. 30 cm$^3$), and saturated bicarbonate (ca. 30 cm$^3$). Ethyl acetate layer was dried over magnesium sulphate and evaporated to dryness to give an orange oil (7.42 g, ~24.70 mmol) [~100% Yield].

$^1$H NMR (CDCl$_3$); 1.30 (3H, t), 1.48 (9H, s), 4.28 (2H, q), 5.68 (1H, br.), 7.88 (1H, s), 8.78 (1H, s).

D,L-(5-Thiazolyl)glycine Ethyl Ester

To a r.b. flask (250 cm$^3$), was added 5-thiazolyl-oximinoacetic acid ethyl ester (6.37 g, 31.825 mmol) to ethanol (c.a. 80 cm$^3$) with stirring. 50% Formic acid solution (50 cm$^3$) was added with zinc dust (5.10 g, 81.83 mmol) and allowed to stir overnight. Reaction monitored by TLC (60% hexane/ethyl acetate; s.m. r.f 0.3, prod. r.f. 0.05.). Reaction solution filtered over diatomaceous earth and filtrate concentrated in vacuo. This was basified to pH 9 with anhydrous potassium carbonate and product taken up in 3:1 chloroform/isopropanol solution (c.a. 200 cm$^3$). This was washed with saturated bicarbonate (c.a. 50 cm$^3$), dried over magnesium sulphate and concentrated in vacuo to give a brown oil (4.60 g, 24.70 mmol) [78% Yield].

1H NMR (CDCl$_3$); 1.25 (3H, t), 1.95 (2H, br.), 4.22 (2H, q), 4.85 (1H, s), 7.80 (1H, s), 8.70 (1H, s).

Intermediate PAE-7

N-Boc-D,L-(4-thiazolyl)glycine ethyl ester

To a solution of D,L-(4-thiazolyl)glycine ethyl ester (0.460 g, 2.470 mmol) in tetrahydrofuran (20 cm$^3$), was added di-tert-butyl dicarbonate (0.530 g, 2.470 mmol) and triethylamnine (0.344 cm$^3$, 2.470 mmol). This was allowed to stir for 1 hour and the solution concentrated in vacuo. The oil was taken up in ethyl acetate (c.a. 50 cm$^3$) washed with 0.5% hydrochloric acid solution (c.a. 20 cm$^3$), and saturated sodium bicarbonate solution (c.a. 20 cm$^3$). This was then dried over magnesium sulphate and concentrated in vacuo to yield an orange oil (0.709 g, 2.477 mmol) [~100% yield].

$^1$H NMR (CDCl$_3$) 1.15 (3H, t), 1.35 (9H, s), 4.1 (2H, m), 5.45 (1H, d); 5.75 (1H, d), 7.3 (1H, d), 8.7 (1H, d).

D,L-(4-Thiazolyl)glycine Ethyl Ester

This was prepared from ethyl-α-oximino-thiazole-4-acetate (0.60 g) using the method of Hatanaka et al. (*Journal of Medicinal Chemistry*, 1973, 16(9), 978–984) to yield the titled compound (0.46 g).

$^1$H NMR (CDCl$_3$) 1.25 (3H, t), 1.8–2.3 (2H, br.), 4.1 (2H, m), 4.75 (1H, s), 7.25 (1H, d), 8.7 (1H, d).

Intermediate PAE-8

N-Boc-D,L-(2-methylthiazol-4-yl)glycine Ethyl Ester

To a solution of D,L-(2-methylthiazol-4-yl)glycine ethyl ester (0.397 g, 1.982 mmol) in tetrahydrofuran (20 cm$^3$), was added di-tert-butyl dicarbonate (0.475 g, 2.180 mmol) and triethylamine (0.304 cm$^3$, 2.180 mmol). This was allowed to stir for 1 hour and the solution concentrated in vacuo. The oil was taken up in ethyl acetate (c.a. 50 cm$^3$) washed with 0.5% hydrochloric acid solution (c.a. 20 cm$^3$), and saturated sodium bicarbonate solution (c.a. 20 cm$^3$). This was then dried over magnesium sulphate and concentrated in vacuo to yield a yellow oil (0.654 g, 2.177 mmol) [~100% yield].

1H NMR (CDCl$_3$) 1.1 (3H, s), 1.35 (9H, s), 2.6 (3H, s), 4.15 (3H, m), 5.3 (1H, d), 5.7 (1H, s), 7.0 (1H, s).

D,L-(2-Methylthiazol-4-yl)glycine Ethyl Ester

This was prepared from ethyl-α-oximino-2-methylthiazole-4-acetate (0.62 g) using the method of Hatanaka et al. (*Journal of Medicinal Chemistry*, 1973, 16(9), 978–984) to yield the titled compound (0.40 g).

$^1$H NMR (CDCl$_3$) 1.15 (3H, t), 1.95 (2H, br.), 2.6 (3H, s), 4.15 (2H, m), 4.65 (1H, s), 6.95 (1H, s).

Intermediate PAE-9

Boc-R-(4-hydroxyphenyl)glycine Methyl Ester

To a stirred mixture of R-(4-hydroxyphenyl)glycine methyl ester hydrochloride (14 g) and sodium bicarbonate (11.7 g) in THF (150 mL) and water (50 mL), was added in one portion, di-t-butyl dicarbonate (15.9 g). The mixture was stirred rapidly to allow thorough mixing for 4 h. Hexane (75 mL) was added and the organic layer separated and washed with satd sodium bicarbonate solution, then brine and then dried with magnesium sulphate. The drying agents was filtered off and washed with a little THF and evaporated to dryness, finishing with a high vacuum pump to remove the last traces of di-t-butyl dicarbonate. Yield 19.7 g, 96%.

$^1$H NMR

R-(4-Hydroxyphenyl)glycine Methyl Ester Hydrochloride

To a dry 250 mL three necked round bottom flask, equipped with a low temperature thermometer, a septum for nitrogen coverage and another for introduction of thionyl chloride by syringe, was added R-4-hydroxyphenylglycine (12.5 g) and dry methanol (24 mL). The mixture was stirred (magnetic stirrer) and cooled to an internal temperature of −20° C. using cardice/acetone. Using a syringe, thionyl chloride was added dropwise to the cooled mixture over a period of 10 min. (Care: the reaction of thionyl chloride with methanol is very exothermic and rate of addition should be such that the thionyl chloride is efficiently stirred into the mixture and that the temperature does not rise above −20° C. Once the addition was complete the mixture was allowed to warm to room temperature overnight (16–18 h). Dry ether (150 mL) was added and the white ppt. that formed was filtered off, washed with a little more ether and dried. Yield 15.5 g, 95%.

$^1$H NMR

Intermediate PAE-10

Boc-R-(4-Trifluoromethanesulphonyloxyphenyl)glycine Methyl Ester Hydrochloride

To a stirred solution of Boc-R-(4-hydroxyphenyl)glycine methyl ester (19 g) in dichloromethane (400 mL) was added 2,6-lutidine (9.44 mL) and 4-dimethylaminopyridine (1.65 g) and the mixture cooled in an ice bath. Trifluoromethanane-sulphonic anhydride (13.74 mL) was added over a period of 5 min, and then the reaction left to warm to room temperature over 4 h. The organic solution was washed with water (2×150 mL), 1 N HCl (2×150 mL), and then saturated sodium bicarbonate (150 mL). The organics were dried with magnesium sulphate and then evaporated to an oil. The mixture was purified using flash chromatography (SiO$_2$ 250 g, eluting with 1:1 hexane/dichloromethane and then neat dichloromethane). Pure product fractions were combined and evaporated, finishing with a high vacuum pump to remove all traces of solvent, to give a white solid, 19 g, 77%.

$^1$H NMR

Intermediate PAE-11

Boc-R-(4-Methoxycarbonylphenyl)glycine Methyl Ester

Method PAE-D

Boc-R-4-trifluoromethanesulphonyloxyphenylglycine methyl ester (15 g), methanol (32.6 mL), bis-1,3-diphenyl-phosphinylpropane (448 mg), palladium (II) acetate (255 mg), triethylamine (10.2 mL) and dimethylformamide (72 mL) were placed in the glass liner of pressure (Parr) reactor and the reactor assembled. The vessel was pressurised to ~0.68 bar (10 psig) with nitrogen and the gas released (repeated five times to remove all oxygen from the system). Carbon monoxide gas was then carefully introduced (use extreme care—the gas cylinder is pressurised to far beyond the bursting disc pressure of the Parr, ideally use a pressure regulator to reduce the pressure to ~6.8 bar, 100 psig) to ~1.4 bar (20 psig) and released three times (into the back of a fume hood). Carbon monoxide was then added to ~6.8 bar (100 psig) and the stirrer started. The vessel was slowly heated to 65° C. internal temperature and then stirred at 65° C. overnight. (At the early stages more carbon monoxide was added to maintain ~6.8 bar, 100 psig.) A sample was removed after 18 h and examined by tlc. When complete, the reaction was cooled to ~30° C., the gas released and the vessel flushed five times with nitrogen as before. The reaction mixture was partitioned between ethyl acetate and water, and the organic layer washed with 1 M hydrochloric acid and then saturated sodium bicarbonate. The solution was dried with MgSO$_4$ and evaporated. Flash chromatography of the resulting oil gave the product, pure by tlc, 10.6 g, 90%.

$^1$H NMR

Intermediate PAE-12

Boc-R-(4-Benzyloxycarbonylphenyl)glycine Methyl Ester

Prepared from Boc-R-4-trifluoromethanesulphonyloxy phenylglycine methyl ester and benzyl alcohol using Method PAE-D $^1$H NMR Intermediate PAE-13

Boc-R-(4-Carboxyphenyl)glycine Methyl Ester

Boc-R-(4-benzyloxycarbonylphenyl)glycine methyl ester (500 mg) was dissolved in THF containing Pd/C 10% (100 mg) and hydrogenated at 1 atm for 2 h. Removal of the catalyst by filtration and evaporation of solvent gave Boc-R-(4-carboxy-phenyl)glycine methyl ester (330 mg, 87%).

$^1$H NMR

Intermediate PAE-14

Boc-R-(4-carboxamidophenyl)glycine Methyl Ester

Method PAE-E

To a solution of Boc-R-(4-carboxyphenyl)glycine methyl ester (3.5 g) in DMF (30 mL) was added EDCI (2.60 g, 1.36 mmol) and HOBt (1.4 g, 10.4 mmol), and the mixture stirred for 10 min before cooling in a ice bath and bubbling in ammonia gas for 5 min. The mixture was stirred for 2 h at room temperature and then diluted with ethyl acetate and washed with water. The aqueous solution was extracted with a little ethyl acetate and the combined organics washed with brine. The organic solution was evaporated to an oil which was purified by flash chromatography (SiO$_2$-dichloromethane/ethyl acetate 0–25%) to give Boc-R-(4-carbox-amidophenyl)glycine methyl ester (1.7 g, 48%).

$^1$H NMR

Intermediate PAE-15

Boc-R-(4-methylcarboxamidophenyl)glycine Methyl Ester

Prepared from Boc-R-(4-carboxyphenyl)glycine methyl ester and methylamine using Method PAE-E.

$^1$H NMR

Intermediate PAE-16

N-4-Methoxybenzoyl-N-2,4-dimethoxybenzyl-D,L-(quinolin-4-yl)glycine Methyl Ester Prepared from quinoline-4-carboxaldehyde using Method PAE-C.

$^1$H NMR

Intermediate PAE-17

Ethyl Boc-D,L-thiazol-2-ylglycine

Prepared from ethyl hydroxyimino-thiazol-2-ylacetate using Method PAE-B. In this case, reaction with Zn/formic acid was conducted over 15 min.

$^1$NMR

IS-MS, m/e 287.0 (M+1)

Intermediate PAE-18

Ethyl Boc-D,L-isoquinolin-8-ylglycine

Prepared from ethyl hydroxyimino-isoquinolin-8-ylacetate using Method PAE-B. In this case, reaction with Zn/formic acid was conducted over 30 min, followed by concentration and partitioning of the residue between 3/1 chloroform/isopropanol and satd aq. NaHCO$_3$. The Boc protection was carried out as previously described. Purification was performed using silica gel chromatography (Biotage Quad System) eluting with 10% ethyl acetate in methylene chloride.

$^1$NMR

IS-MS, m/e 331.0 (M+1)

Analysis for $C_{18}H_{22}N_2O_4$:

Calcd: C, 65.44; H, 6.71; N, 8.48;

Found: C, 65.05; H, 6.67; N, 8.49.

Preparation of Intermediates PAA-1–PAA-28

The following compounds were prepared according to the indicated method (Method PAA-A, Method PAA-B, Method PAA-C, Method PAA-D, Method PAA-E or Method PAA-F) from the indicated starting materials, unless otherwise described.

Intermediate PAA-1

Boc-D,L-(2-chlorophenyl)glycine

Method PAA-A

2-Chlorobenzaldehyde (20 mmol, 2.252 mL) and 2,4-dimethoxybenzylamine (20 mmol, 3.004 mL) were added together and stirred for 2 hours. DCM (5 mL) was added and any water separated and removed. tert-Butyl isonitrile (20 mmol, 2.262 mL) was added and stirred for 10 min, followed by acetic acid (20 mmol, 1.145 mL). Stirring was continued for 3 days. The reaction mixture was then treated with TFA (30 mL) and triethylsilane (5 mL). After 3 h the mixture was evaporated to dryness, 6 M HCl (100 mL) added, and the whole refluxed overnight at 130° C., stirring rapidly. The mixture was allowed to cool and extracted with EtOAc (50 mL×2); the aqueous fraction was evaporated to dryness and treated with 2 M NaOH solution. The mixture was extracted with EtOAc (50 mL×2); excess boc anhydride (5.2 g) in dioxane (20 mL) was added to the aqueous fraction and stirred overnight. The mixture was extracted with diethyl ether (100 mL×2), acidified to pH 1 (conc HCl) and extracted with EtOAc (50 mL×2). The combined organic fractions were washed with water and evaporated to dryness under high vacuum. The product Boc-2-chlorophenylglycine (4.252 g, 74.5%)

$^1$H NMR (CD$_3$CN/D$_2$O) 7.3 (4H, m); 5.5 (1H, s); 1.3 (9H, s). MS 286 (M+1)

Intermediate PAA-1'
(R)-Benzyloxycarbonyl-(2-chlorophenyl)glycine

Prepared from 2-chlorostyrene using the method of Sharpless et al J.A.C.S. (1998) Vol120 No. 6 1207–1217.

Intermediate PAA-1, Alternative Preparation
Boc-D,L-(2-chlorophenyl)glycine

Prepared from 2-chlorobenzaldehyde using method PAA-F. In this case, the reaction temperature was not controlled upon addition of 2-chlorobenzaldehyde and the reaction was allowed to stir for 2 h. Extraction of the intermediate aminonitrile was performed with ethyl ether in place of ethyl acetate and was further purified by addition of HCl gas to the ethereal extracts followed by decantation of the mother liquor to isolate the semisolid hydrochloride salt. BOC protection of the amino acid was performed from 0° C. to room temperature over a period of one hour and the final extraction was performed with ethyl acetate in place of ethyl ether.

$^1$H-NMR
IS-MS m/e 284 (M−1)

Intermediate PAA-2
Boc-D,L-(3-fluorophenyl)glycine

Prepared from 3-fluorobenzaldehyde using Method PAA-A.

$^1$H NMR (CD$_3$CN/D$_2$O) 7.3 (1H, m), 7.1 (3H, m); 5.2 (1H, s); 1.3 (9H, s). MS 270 (M+1)

Intermediate PAA-3
Boc-D,L-(4-fluorophenyl)glycine

Prepared from 4-fluorobenzaldehyde using Method PAA-A.

$^1$H NMR (CD$_3$CN/D$_2$O) 7.3 (2H, m); 6.9 (2H, m), 5.0 (1H, s); 1.3 (9H, s). MS 270 (M+1)

Intermediate PAA-4
Boc-D,L-(2-methylphenyl)glycine

Prepared from 2-methylbenzaldehyde using Method PAA-A.

$^1$H NMR (CD$_3$CN/D$_2$O) 7.3 (4H, m); 5.5 (1H, s); 2.5 (3H, s); 1.3 (9H, s). MS 266 (M+1)

Intermediate PAA-5
Boc-D,L-(3-thienyl)glycine

Prepared from 3-thiophenecarboxaldehyde using Method PAA-A.

$^1$H NMR (CD$_3$CN/D$_2$O) 7.5 (2H, m); 7.1 (1H, d); 5.3 (1H, s); 1.3 (9H, s). MS 258 (M+1)

Intermediate PAA-6
Boc-D,L-(2-fluorophenyl)glycine

Was obtained by treating D,L-2-fluorophenylglycine (Aldrich) with Boc anhydride (1.1 eq) and 2 M NaOH (1 eq) in ethanol. Aqueous work up as described above yielded the protected amino acid.

$^1$H NMR

Intermediate PAA-7
Boc-D,L-(2-methoxyphenyl)glycine

Prepared from 2-methoxybenzaldehyde using Method PAA-A.

$^1$H NMR

Intermediate PAA-7, Alternative Preparation
Boc-D,L-(2-methoxyphenyl)glycine

Prepared from 2-methoxybenzaldehyde using method PAA-F. In this case, the reaction was cooled to 0° C. before addition of 2-methoxybenzaldehyde and was then allowed to stir at room temperature overnight. Extraction of the intermediate aminonitrile was performed with ethyl ether in place of ethyl acetate and was further purified by addition of 1 M HCl in ethyl ether followed by filtration of the crystalline hydrochloride salt. BOC protection of the amino acid was performed from 0° C. to room temperature over a period of three hours, and the final extraction was performed with dichloromethane in place of ethyl ether.

$^1$H-NMR
IS-MS m/e 280.1 (M−1)
Analysis for C$_{14}$H$_{19}$NO$_5$
Calcd: C, 59.78; H, 6.81; N, 4.98;
Found: C, 59.68; H, 6.78; N, 4.95.

Intermediate PAA-8
Boc-D,L-(2-trifluoromethyl)phenylglycine.

Prepared from 2-trifluoromethylbenzaldehyde using Method PAA-A.

$^1$H NMR

Intermediate PAA-8, Alternative Preparation
Boc-D,L-(2-trifluoromethylphenyl)glycine Prepared from 2-trifluoromethylbenzaldehyde using method PAA-F. In this case, the reaction temperature was not controlled upon addition of 2-trifluoromethylbenzaldehyde and the reaction was allowed to stir for 2 h. Extraction of the intermediate aminonitrile was performed with ethyl ether in place of ethyl acetate and was further purified by addition of HCl gas to the ethereal extracts followed by decantation of the mother liquor to isolate the semisolid hydrochloride salt. BOC protection of the amino acid was performed from 0° C. to room temperature over a period of one hour and the final extraction was performed with ethyl acetate in place of ethyl ether.

$^1$H-NMR
IS-MS m/e 318 (M−1)

Intermediate PAA-9
Boc-D,L-(8-quinolinyl)glycine

Method PAA-B

To a stirring solution of Boc-D,L-(8-quinolinyl)glycine ethyl ester (2.29 g, 6.93 mmol) in 1,4-dioxane (11 mL) was added a solution of LiOH hydrate (0.32 g, 7.6 mmol) in water. After 2 h, the solvents were removed in vacua and the residue was dissolved in water and washed with diethyl ether. The aqueous phase was then acidified to pH 3 with solid citric acid and extracted with ethyl acetate. The organic phase was then washed with brine, dried with Na$_2$SO$_4$, filtered and concentrated to give 2.06 g (98%) of the title compound.

$^1$H-NMR
IS-MS, m/e 303.0 (M+1)

Intermediate PAA-10
Boc-D,L-(5-quinolinyl)glycine

Prepared from Boc-D,L-(5-quinolinyl)glycine ethyl ester using Method PAA-B.

1H-NMR
IS-MS, m/e 303.0 (M+1)

Intermediate PAA-11
Boc-D-(3-bromophenyl)glycine

Prepared from R-3-bromo-(1-t-butoxycarbonylamino-2-hydroxyethyl)benzene using Method PAA-C.

Melting Point=130–132° C. with decomposition
$^1$H NMR (CDCl$_3$)
API-MS, m/e=286 (M−CO$_2$H+1)

Intermediate PAA-12
Boc-D-(3-methoxycarbonylphenyl)glycine

Method PAA-C

To a stirred solution of R-3-methoxycarbonyl-(1-t-butoxycarbonylamino-2-hydroxyethyl)benzene (338 mg, 1.14 mmol) in acetone (7.2 mL) was added 5% NaHCO$_3$ (3 mL). The reaction mixture was cooled to 0° C. To the stirred suspension was added KBr (14 mg, 0.12 mmol), TEMPO (181 mg, 1.16 mmol) and NaOCl dropwise (2.81 mL, 5.25%). After 1 h at 0° C., TEMPO (136 mg, 0.88 mmol) and NaOCl (1.09 mL; 5.25%) were added. The reaction was stirred for a further 0.5 h at 0° C. and 5% NaHCO$_3$ (4.3 mL) was added. The reaction was allowed to warm to room temperature overnight. Acetone was removed under vacuum and the crude product was partitioned between ethyl acetate and water. The aqueous layer was washed with ethyl acetate (2×) and acidified to pH 5 with 10% citric acid and extracted with ethyl acetate (4×). The combined organic extracts were dried over MgSO$_4$. Removal of solvent under vacuum gave the product (305 mg, 86%).

$^1$H NMR (CDCl$_3$)

API-MS, m/e=254 (M–C$_4$H$_9$+1)

Intermediate PAA-13

Boc-D-(3-cyanophenyl)glycine

Prepared from R-3-cyano-(1-t-butoxycarbonylamino-2-hydroxyethyl)benzene using Method PAA-C.

$^1$H NMR (CDCl$_3$)

API-MS, m/e=221 (M–C$_4$H$_9$+1)

Intermediate PAA-14

Boc-D-(3-ethanesulfonylaminophenyl)glycine

To a stirring solution of 3-(ethanesulfonylaminophenyl) glycine (20 g, 77.43 mmol) and sodium carbonate (8.2 g, 77.43 mmol) in 3:1 THF:water (200 mL) at 0° C., was added di-tert-butyl dicarbonate (18.5 g, 85.17 mmol). After stirring for 30 min, the cold bath was removed; and after an additional 30 min at room temperature the solvent was removed; and the residue was partitioned between ethyl acetate and water. The aqueous layer was acidified to pH 2 with KHSO$_4$ and extracted twice with ethyl acetate. The combined ethyl acetate extracts were washed with water, dried with Na$_2$SO$_4$, filtered and concentrated in vacuo to give 17.51 g (63%) of a white solid.

1H-NMR

IS-MS, m/e 357.0 (M–1)

Intermediate PAA-15

N-Boc-D,L-(5-thiazolyl)glycine

To a r.b. flask (150 cm$^3$), was added Boc-D,L-(5-thiazolyl)glycine ethyl ester (7.00 g, 24.70 mmol) to ethanol (c.a. 100 cm$^3$) with stirring. 2 M Sodium hydroxide solution (25 cm$^3$, 50 mmol) was added and allowed to stir for 1 h. Reaction monitored by TLC (60% hexane/ethyl acetate; s.m. r.f 0.5, prod. r.f. 0.). Reaction concentrated in vacuo and product taken up in saturated bicarbonate (c.a. 50 cm$^3$) and washed with ethyl acetate (c.a. 30 cm$^3$). Aqueous layer was acidified to pH 2 with concentrated hydrochloric acid and product extracted with 3:1 chloroform/isopropanol solution (c.a. 3×60 cm$^3$). The organic layer was dried over magnesium sulphate and evaporated to dryness to give an orange solid (4.47 g, 17.30 mmol) [74% Yield].

$^1$H NMR (CDCl$_3$); 1.35 (9H, s), 5.60 (1H, d), 5.83 (1H, d), 7.88 (1H, s), 8.80 (1H, s).

Intermediate PAA-16

N-Boc-D,L-(4-thiazolyl)glycine

Method PAA-D

To a solution of N-Boc-D,L-(4-thiazolyl)glycine ethyl ester (0.700 g, 2.470 mmol) in methanol (c.a. 15 cm$^3$), was added 2 M sodium hydroxide (2.47 cm$^3$, 4.940 mmol) and allowed to stir for 90 min. The solution was concentrated in vacuo and taken up in water (c.a. 20 cm$^3$). The aqueous solution was washed with ethyl acetate (c.a. 20 cm$^3$), and then acidified to pH 2 with 5% hydrochloric acid solution (c.a. 50 cm$^3$). The product was extracted with ethyl acetate (c.a. 3×30 cm$^3$), dried over magnesium sulphate, and concentrated in vacuo to yield a pale yellow oil (0.582 g, 2.254 mmol) [91% yield].

$^1$H NMR (CDCl$_3$) 1.35 (9H, s), 5.5 (1H, d), 5.8 (1H, d), 7.35 (1H, d), 8.75 (1H, d), 9.8–10.2 (1H, br.).

Intermediate PAA-17

N-Boc-D,L-(2-methylthiazol-4-yl)glycine

Prepared from N-Boc-D,L-(2-methylthiazol-4-yl)glycine ethyl ester using Method PAA-D.

$^1$H NMR (CDCl$_3$) 1.35 (9H, s), 2.6 (3H, s), 5.4 (1H, d), 5.9 (1H, s), 7.1 (1H, s).

Intermediate PAA-18

N-Boc-D,L-(2-Benzyloxycarbonylamino-4-thiazolyl) glycine

Is prepared from D,L-(2-benzyloxycarbonylamino-4-thiazolyl)glycine. The benzyloxycarbonyl protecting group is removed from the thiazolyl amino group at a convenient point in the preparation of a final compound using a conventional method, such as, for example, heating a solution of an intermediate in HBr/acetic acid at 60° C., followed by evaporation and a conventional isolation, such as by using SCX ion exchange chromatography.

D,L-(2-Benzyloxycarbonylamino-4-thiazolyl)glycine

Was prepared by the method of Hardy, K.; Harrington, F. and Stachulski, A.-J. Chem. Soc. Perkin Trans I (1984) 1227–1235.

Intermediate PAA-19

Boc-R-(4-methoxycarbonylphenyl)glycine

To a solution of Boc-R-(4-methoxycarbonylphenyl) glycine methyl ester (692 mg) in THF (10 mL) was added a solution of lithium hydroxide hydrate (90 mg) in water (7 mL). The mixture immediately became cloudy and over 15 min cleared. After 30 min, tlc showed the reaction to be complete. Ethyl acetate (20 mL) and water (20 mL) were added, and the aqueous layer separated. The aqueous solution was acidified with 2 M hydrochloric acid and extracted with ethyl acetate (3×20 mL). The organic solution was then washed with water×2 and brine×2, dried with MgSO$_4$ and evaporated to give the mono-ester (650 mg, 98%), pure by tlc.

$^1$H NMR

Intermediate PAA-20

Boc-R-(4-Methoxyphenyl)glycine

Boc-R-(4-hydroxyphenyl)glycine methyl ester was converted to Boc-R-4-methoxyphenylglycine using the alkylation method described by Basak et al. (Tetrahedron Lett. 1998, 39 (27), 4883–4886), followed by hydrolysis of the methyl ester with lithium hydroxide in aqueous THF.

$^1$H NMR

Intermediate PAA-21

N-4-Methoxybenzoyl-N-2,4-dimethoxybenzyl-D,L-(2-trifluoro-methylphenyl)glycine

Prepared from N-4-methoxybenzoyl-N-2,4-dimethoxybenzyl-D,L-(2-trifluoromethylphenyl)glycine methyl ester using Method PAA-B (3 equivalents of LiOH hydrate).

$^1$H NMR

IS-MS, m/e 503.9 (m+1)

Intermediate PAA-22

N-4-Methoxybenzoyl-N-2,4-dimethoxybenzyl-D,L-(thien-2-yl)-glycine

Method PAA-E

To a solution of 2-thipheneboronic acid (5.0 g, 39.0 mmol, 1 equiv) in 275 mL of methylene chloride at rt was added 3,4-dimethoxybenzylamine (5.89 mL, 39.0 mmol, 1 equiv) followed by glyoxylic acid monohydrate 3.6 g, 39 mmol, 1 equiv). The reaction was allowed to stir for 56 hours at rt after which time the resultant precipitate was filtered and washed with methylene chloride to afford 9.3 g (78%) of N-2,4-dimethoxybenzyl-D,L-(thien-2-yl)glycine as an off-white solid (IS-MS, m/e 308 (m+1)).

A portion of the solid (5.0 g, 16.3 mmol, 1 equiv.) was dissolved in acetone (20 mL) and 1 N sodium hydroxide (20 mL) at rt. To this solution was simultaneously added anisoyl chloride (2.78 g, 16.3 mmol, 1 equiv.) in 20 mL of acetone and 2 N sodium hydroxide in dropwise fashion. After stirring at rt for 1 h, the reaction was cooled to 0° C. and was acidified to pH 2–3. Diethyl ether was added and the product was extracted into the organic phase. The combined organic phases were washed with brine, dried over sodium sulfate, filtered, and concentrated to afford 5.1 g (71%) of the titled compound as a white solid.

IS-MS, m/e 440 (m+1).

Intermediate PAA-23

N-Boc-N-2,4-dimethoxybenzyl-D,L-(thien-2-yl)glycine

To a solution of N-2,4-dimethoxybenzyl-D,L-(thien-2-yl) glycine (1.0 g, 3.2 mmol, 1 equiv) in 6 mL of acetone and 6 mL of water at rt was added triethylamine (0.97 mL, 7.0 mmol, 2.1 equiv.) followed by addition of 2-(tert-butoxy-carbonyloxyimino)-2-phenylacetonitrile (BOC-ON) (0.76 g, 3.1 mmol, 0.95 equiv). After stirring at rt overnight, the reaction was diluted with water and washed with ether. The aqueous phase was then acidified with 0.5 M citric acid and the product was extracted into diethyl ether. The combined organic phases were washed with brine, dried over sodium sulfate, filtered, and concentrated to afford 0.38 g (29%) of the titled compound as a crude yellow oil.

IS-MS, m/e 408 (m+1).

Intermediate PAA-24

Boc-D,L-isoquinolin-8-ylglycine

Prepared from ethyl Boc-D,L-isoquinolin-8-ylglycine using Method PAA-B. The product was precipitated from a basic aqueous solution by adjusting the pH to 3 with solid citric acid.

$^1$NMR

IS-MS, m/e 303.0 (M+1)

Analysis for $C_{16}H_{18}N_2O_4 \cdot 0.5\ H_2O$:

Calcd: C, 61.73; H, 6.15; N, 9.00;

Found: C, 61.62; H, 5.66; N, 8.84.

Intermediate PAA-25

Boc-D,L-Naphthalen-1-ylglycine

Method PAA-F

Part A: D,L-Naphthalen-1-ylglycine hydrochloride

To a solution of sodium cyanide (10.0 g, 0.22 mmol) in 40 mL of water was added ammonium chloride (11.4 g, 0.22 mmol), and the mixture was stirred until dissolution was complete. A solution of 1-naphthaldehyde (31.0 g, 0.22 mmol) in 40 mL of methanol was then added and the resultant mixture was allowed to stir at room temperature for two days. An additional 150 mL of water was then added and the crude product was extracted into EtOAc. The combined organic layers were washed with water, dried over $Na_2SO_4$, filtered and concentrated to afford a crude oil. The crude residue was chromatographed over silica gel, eluting with with 10:1 EtOAc:$CH_2Cl_2$, to give 35 g of a light brown oil. This material was then dissolved in 250 mL of 5 N HCl and was heated to reflux for 9 h. The reaction was allowed to cool to room temperature and the product was allowed to crystallize overnight. Filtration of the mixture afforded 13.6 g (29%) of the title compound as light brown crystals.

$^1$NMR

IS-MS, m/e 201.9 (M+1)

Part B: Boc-D,L-Naphthalen-1-ylglycine

To a solution of D,L-naphthalen-1-ylglycine hydrochloride (13.6 g, 57.2 mmol) and 2 N sodium hydroxide (57 mL, 115 mmol) in 120 mL of 1,4-dioxane and 60 mL of water was added $(Boc)_2O$ (15 g, 69 mmol). The reaction was allowed to stir at room temperature for 3 h after which time the solution was brought to pH 5 by addition of 1 N sulfuric acid. The product was then extracted into EtOAc; and the combined organic extracts were dried over $Na_2SO_4$, filtered, and concentrated to give 14 g (81%) of the title compound as a light brown foam.

$^1$NMR

IS-MS, m/e 300.1 (M–1)

Intermediate PAA-26

Boc-D,L-(2-methylthiophenyl)glycine

To a solution of 2-(methylthio)benzaldehyde (15 g, 98.7 mmol) in 100 mL of ethanol was added ammonium carbonate (23.1 g, 296 mmol) and a solution of potassium cyanide (12 g, 148 mmol) in 100 mL water. The reaction was heated and stirred at 70° C. for 3 h after which time the reaction was concentrated under reduced pressure. The product was extracted into ethyl acetate; and the combined organic phases were washed with brine, dried over $Na_2SO_4$, filtered and concentrated. The resultant crude residue was taken up in 70 mL of ethyl acetate, and 70 mL of 5 N sodium hydroxide was added. The reaction was heated to reflux for three days after which time the ethyl acetate was removed under reduced pressure. To the aqueous mixture was sequentially added 100 mL of dioxane, $Boc_2O$ (42 g, 192 mmol), and 100 mL of 2.5 N sodium hydroxide. The reaction was then heated at reflux for 48 h. After cooling to room temperature, the reaction was diluted with water and the aqueous phase was washed with ethyl ether. The aqueous layer was then acidified to pH 2 and the product was extracted into ethyl acetate. The combined organic extracts were washed with brine, dried over $MgSO_4$, filtered, and concentrated to afford 21.7 g of a crude residue. Purification by silica gel chromatography (gradient elution, 97:2:1 to 95:4:1 dichloromethane:methanol:acetic acid) provided 5.0 g (17%) of the title compound.

$^1$H-NMR

ES-MS m/e 296 (M–1)

Intermediate PAA-27

Boc-D,L-(2-methylsulfonylphenyl)glycine

To a solution of boc—D,L-(2-methylthiophenyl)glycine (4.5 g, 15.2 mmol) in 75 mL of methanol was added a solution of oxone (14 g, 23 mmol) in water. The reaction was stirred at room temperature for 2 h after which time the methanol was removed under reduced pressure. The product was extracted into ethyl acetate and the combined organic layers were washed with brine, dried over $MgSO_4$, filtered, and concentrated to afford 4.35 g (87%) of the title compound.

$^1$H-NMR

ES-MS m/e 230(M+1–$C_5H_9O_2$)

Intermediate PAA-28

Boc-D,L-(benzo[b]thiophen-3-yl)glycine

May be prepared by the method of Kukolja, S. et al. *J. Med. Chem.* 1985, 28, 1886–1896.

General Experimental Procedures: Synthesis of Inhibitors

Coupling Method A

The coupling of an amine and carboxylic acid to form an amide. A solution of the amine (1 equiv) and carboxylic acid (1.1 equiv) in a suitable solvent (DMF, and/or methylene chloride) is or was treated with diethyl cyanophosphonate (1.1 equiv) followed by addition of triethylamine or diisopropylethyl amine (0 to 3 equiv) to the mixture. After completion of the reaction by thin-layer chromatography, the mixture was partitioned between a suitable solvent (EtOAc, and/or methylene chloride) and washed with 1 N NaOH, water, brine, and concentrated. The crude mixture was then purified, as indicated, or used directly in subsequent transformations.

Coupling Method B

The coupling of an amine and carboxylic acid to form an amide. A solution of the amine (1 equiv) and carboxylic acid (1.1 equiv) in a suitable solvent (DMF, and/or methylene chloride) is or was treated with a carbodiimide-based dehydrating agent (e.g. DCC, or EDCI) (1.0 equiv). In general, addition of a benzotriazole-based reagent (e.g. HOBT or HOAT) (1 equiv) improved reaction yields. After completion of the reaction by thin-layer chromatography, the mixture is or was partitioned between a suitable solvent (EtOAc, and/or methylene chloride) and washed with 1 N NaOH, water, brine, and concentrated. The crude mixture is or was then purified, as indicated, or used directly in subsequent transformations.

Coupling Method C

The coupling of an amine and acid chloride to form an amide. A solution of the amine (1 equiv) in an appropriate solvent (chloroform, and/or methylene chloride) and pyridine (1–10 equiv) is or was treated with an acid chloride (1.1 equiv). After completion of the reaction by thin-layer chromatography, the mixture is or was partitioned between a suitable solvent (EtOAc, methylene chloride, and/or chloroform) and washed with 1 N NaOH, water, brine, and concentrated. The crude mixture is or was then purified, as indicated, or used directly in subsequent transformations.

Deprotection Method A

A mixture of 10% Palladium on carbon and the starting material in an appropriate solvent (EtOAc, EtOH, and/or HOAc) is or was placed under an atmosphere of hydrogen. Upon completion, the mixture is or was filtered and the resulting filtrate concentrated. The crude mixture is or was then purified, as indicated, or used directly in subsequent transformations.

Alkylation Method A

A solution of the starting material (1 equiv) in 5–10% HOAc in methanol (anhydrous) is or was treated with the indicated aldehyde or ketone (2–10 equiv) followed by sodium cyanoborohydride (2–10 equiv). After completion, the mixture is or was concentrated and the residue was either partitioned between a suitable solvent (EtOAc, methylene chloride, and/or chloroform) and washed with 1 N NaOH, water, brine, and concentrated or directly loaded onto an ion-exchange resin (SCX, Varian) and eluted with methanol followed by 2 N ammonia in methanol. Concentration of the later fractions afforded the free base product. The crude mixture is or was then purified, as indicated, or used directly in subsequent transformations.

Preparation of Starting Materials 1-(Benzyloxycarbonyl-D-phenylglycinyl)piperidine-4-methanol (Coupling Method A): A solution of benzyloxycarbonyl-D-phenylglycine (5.0 g, 17.5 mmol) and 4-piperidinemethanol (1.83 g, 15.9 mmol) in 90 mL of methylene chloride was cooled in a methanol/ice bath and then treated with diethyl cyanophosphonate (2.67 mL, 17.5 mmol) followed by ethyl diisopropylamine (3.1 mL). After 5 h, the mixture was concentrated, diluted with EtOAc and saturated aqueous potassium carbonate, and the resulting layers separated. The organic layer was washed (with aqueous potassium carbonate, 1 N HCl, brine), dried over magnesium sulfate, filtered, concentrated, and the residue purified by column chromatography (SiO$_2$: 70%–80% EtOAc:hexane), affording 1.54 g (25%) of the title compound.

$^1$NMR

IS-MS, m/e 725 (M+1)

Analysis for $C_{22}H_{26}N_2O_4 \cdot 0.15\ H_2O$:

Calcd: C, 68.6; H, 6.9; N, 7.3;

Found: C, 68.5; H, 6.9; N, 7.1.

1-(D-Phenylglycinyl)piperidine-4-methanol

Using Deprotection Method A, 1-(benzyloxycarbonyl-D-phenylglycinyl)piperidine-4-methanol (3.93 g, 29.5 mmol) and 10% palladium on carbon (1.30 g) in 2:1 EtOAc:EtOH (75 mL) afforded 2.31 g (88%) of the title compound.

$^1$NMR

IS-MS, m/e 249 (M+1).

Preparation of Intermediates A-1–A-3

Intermediate A-1

1-(4-Methoxybenzoyl-D-phenylglycinyl)piperidine-4-methanol

Using Coupling Method C, 1-(D-phenylglycinyl)piperidine-4-methanol (1.23 g, 4.96 mmol) and p-anisoyl chloride (0.888 g, 5.21 mmol) afforded, after purification by column chromatography (SiO$_2$: 1:1 to 1:9 hexanes:EtOAc), 1.26 g (66%) of the title compound.

$^1$NMR

IS-MS, m/e 383 (M+1)

Intermediate A-2

1- (Indole-6-carbonyl-D-phenylglycinyl)piperidine-4-methanol

Coupling Method B

A solution of 1-(D-phenylglycinyl) piperidine-4-methanol (500 mg, 2.02 mmol), indole-6-carboxylic acid (325 mg, 2.02 mmol), and 1-hydroxy-7-azabenzotriazole (275 mg, 2.02 mmol) in 10 mL of DMF was treated with DCC (415 mg, 2.02 mmol). After 15 h, the mixture was concentrated and the residue dissolved in EtOAc. The organic layer was washed (with 2 N NaOH, water, brine), dried over magnesium sulfate, and concentrated. The residue was purified by column chromatography (SiO$_2$: EtOAc), affording 780 mg (98%) of the title compound.

$^1$NMR

IS-MS, m/e 383 (M+1).

Intermediate A-3

1-(3-Chloroindole-6-carbonyl-D-phenylglycinyl)piperidine-4-methanol

Using Coupling Method B. 1-(D-phenylglycinyl) piperidine-4-methanol (9.90 g, 39.9 mmol) and 3-chloroindole-6-carboxylic acid (8.56 g, 43.9 mmol) afforded, after purification by column chromatography (SiO$_2$: 95% EtOAc in hexane), 8.95 g (53%) of the title compound.

$^1$NMR

IS-MS, m/e 426 (M+1).

Preparation of Intermediate B-1

Intermediate B-1

1-(4-Methoxybenzoyl-D-phenylglycinyl)piperidine-4-carboxaldehyde

A solution of 1-(4-methoxybenzoyl-D-phenylglycinyl)-piperidine-4-methanol (0.800 g, 2.08 mmol) and N-methylmorpholine oxide (0.366 g, 3.13 mmol) in methylene chloride (15 mL) was treated with tetrapropylammonium perruthenate (TPAP, 2 mg). After 14 h, the mixture was treated with additional TPAP (5 mg). After 20 h, the mixture was treated with additional TPAP (5 mg). After 32 h, the mixture was loaded directly onto a column and purified by column chromatography (SiO$_2$: 1:1 to 1:4 hexanes:EtOAc) affording 0.286 g (36%) of the title compound.

$^1$NMR

IS-MS, m/e 381 (M+1).

Preparation of Intermediates C-2–C-4

Intermediate C-2

1-(Indole-6-carbonyl-D-phenylglycinyl)-4-(methylsulfonyl-oxymethyl)piperidine

A solution of 1-(indole-6-carbonyl-D-phenylglycinyl) piperidine-4-methanol (2.82 g, 7.21 mmol) and triethylamine (2.0 mL) in 40 mL of methylene chloride was treated with methanesulfonyl chloride (1.1 mL, 14.0 mmol). After 2 h, mixture was concentrated and the residue purified by column chromatography (SiO$_2$: 90% EtOAc in hexane) to afford 2.80 g (83%) of the title compound.

$^1$NMR

IS-MS, m/e 470 (M+1).

Intermediate C-3

1-(3-Chloroindole-6-carbonyl-D-phenylglycinyl)-4-(methylsulfonyloxymethyl)piperidine.

Using a procedure similar to that described above for Intermediate C-2, 1-(3-chloroindole-6-carbonyl-D-phenylglycinyl)piperidine-4-methanol (8.95 g, 21.0 mmol) afforded, after purification by column chromatography (SiO$_2$: 80% to 99% EtOAc in hexane), 2.58 g (24%) of the title compound.

$^1$NMR

IS-MS, m/e 504 (M+1).

(Protected) Intermediate C-4

1-(1-Methylsulfonyl-3-chloroindole-6-carbonyl-D-phenylglycinyl)-4-(methylsulfonyloxymethyl)piperidine.

Using a procedure similar to that described above for Intermediate C-3, 1-(,3-chloroindole-6-carbonyl-D-phenylglycinyl)piperidine-4-methanol (8.95 g, 21.0 mmol) afforded, as a minor side product after purification by column chromatography (SiO$_2$: 80% to 99% EtOAc in hexane), 940 mg (8%) of the title compound.

$^1$NMR

IS-MS, m/e 582 (M+1)

Preparation of Intermediate D-1

4-(Piperidin-1-ylmethyl)piperidine bis-Hydrochloride Salt

A solution of 4-(piperidin-1-ylmethyl)pyridine (10.0 g, 0.056 mol; prepared using a similar procedure to that described in US430491) and platinum oxide (1.5 g) in 55 mL of ethanol and 18 mL of 12 N HCl was placed under an atmosphere of hydrogen (4.1 bar, 60 psig). After 15 h, the mixture was filtered, concentrated, and residue triturated with methanol affording 9.0 g of the title compound as a bis hydrochloride salt.

$^1$NMR

IS-MS, m/e 183 (M+1).

1-(Benzyloxycarbonyl-D-phenylglycinyl)-4-[(piperidin-1-yl)methyl]piperidine

Using Coupling Method A, benzyloxycarbonyl-D-phenylglycine (17.1 g, 60.1 mmol) and 4-(piperidin-1-ylmethyl)piperidine (10.0 g, 54.6 mmol) afforded, after purification by column chromatography (SiO$_2$: 2% to 3% [2 N ammonia in methanol]:methylene chloride) 10.7 g (43%) of the title compound.

$^1$NMR

IS-MS, m/e 451 (M+1).

Analysis for C$_{27}$H$_{35}$N$_3$O$_3$:

Calcd: C, 72.1; H, 7.8; N, 9.3;

Found: C, 72.0; H, 7.7; N, 9.4.

Intermediate D-1

1-(D-Phenylglycinyl)-4-[(piperidin-1-yl)methyl]piperidine

Using Deprotection Method A, 1-(benzyloxycarbonyl-D-phenylglycinyl)-4-[(piperidin-1-yl)methyl]piperidine (10.7 g, 23.8 mmol) and 10% palladium on carbon (1.35 g) in 200 mL of 1:1 EtOH:EtOAc afforded the title compound.

$^1$NMR

IS-MS, m/e 315 (M+1).

Preparation of Intermediate D-2

1-[Boc-D,L-(2-methoxyphenyl)glycinyl]-4-[(piperidin-1-yl)-methyl]piperidine

Using Coupling Method B, Boc-D,L-(2-methoxyphenyl) glycine (2.0 g, 7.11 mmol) and 4-(piperidin-1-ylmethyl) piperidine (1.43 g, 7.82 mmol) with triethylamine (1 mL, 7.8 mmol) afforded, after purification by column chromatography (SiO$_2$; 0–2% [2 N ammonia in methanol]:methylene chloride), 1.59 g (50%) of the title compound.

$^1$NMR

IS-MS, m/e 446.1 (M+1)

Intermediate D-2

1-[D,L-(2-Methoxyphenyl)glycinyl]-4-(piperidin-1-ylmethyl)piperidine

To a stirring solution of 1-(Boc-D,L-2-methoxyphenyl) glycinyl-4-(piperidin-1-ylmethyl)piperidine (1.52 g, 3.42 mmol) in methylene chloride (15 mL) was added anisole (2.6 mL, 24 mmol) followed by trifluoroacetic acid (5.3 mL). After stirring for 3 h, the solvent was removed in vacuo and the residue was dissolved a minimal volume of methanol and loaded onto an SCX column. The column was eluted with methanol, followed by 2 N ammonia in methanol. The product containing fractions were combined and concentrated in vacuo to give 1.2 g (100%) of the title compound.

$^1$NMR

IS-MS, m/e 346.1 (M+1)

Preparation of Intermediate D-3

1-(Boc-D,L-thiazol-5-ylglycinyl)-4-[(piperidin1-yl) methyl]-piperidine

To a solution of N-Boc-D,L-(5-thiazolyl)glycine (1.36 g, 5.25 mmol), HOAT (787 mg 5.78 mmol), 4-(1-piperidinylmethyl)piperidine (1.35 g 5.25 mmol) and triethylamine (1.61 mL, 11.6 mmol) in DMF (42 mL) was added EDCI (1.11 g, 5.78 mmol) and the mixture stirred at room temperature for 20 h. The solvent was removed in vacuo, the residues taken up in chloroform:isopropyl alcohol (2:1) and washed with water and satd sodium bicarbonate. The aqueous phase was back extracted with chloroform:isopropyl alcohol (2:1) (×2), and the combined organic extracts were dried (MgSO$_4$) and concentrated in vacuo to an orange-brown oil. The crude reaction product thus obtained was carried on to the next step without further purification.

Intermediate D-3

1-(D,L-thiazol-5-ylglycinyl)-4-[(piperidin-1-yl)methyl]-piperidine

To a stirred solution of crude 1-(Boc-D,L-thiazol-5-ylglycinyl)-4-[(piperidin-1-ylmethyl)piperidine] (circa 5.25 mmol) and anisole (11.4 mL) in dichloromethane (42 mL) at room temperature was added TFA (10.5 mL) and the mixture stirred at room temperature for 20 h before concentrating in vacuo. The product was isolated using SCX ion exchange chromatography.

$^1$NMR

Preparation of Intermediate D-4

1-[N-Boc-D,L-(2-benzyloxycarbonylaminothiazol-4-yl) glycinyl]-4-[(piperidin-1-yl)methylpiperidine]

This was prepared by coupling N-Boc-D,L-(2-benzyloxycarbonylamino-4-thiazolyl)glycine and 4-(1- piperidinylmethyl)piperidine as described above in the corresponding step in the preparation of Intermediate D-3.

Intermediate D-4
1-(D,L-2-Aminothiazol-4-ylglycinyl)-4-[(piperidin-1-yl)methyl]piperidine]

A stirred solution of 1-[N-Boc-D,L-(2-benzyloxycarbonylamino-4-thiazolylglycinyl)-4-[(piperidin-1-yl)-methyl)piperidine] (crude, circa 5.25 mmol) in a mixture of HBr-acetic acid (50%, 35 mL) and acetic acid (70 mL) was heated at 60° C. for 7 h, cooled and then concentrated in vacuo. The product was isolated using SCX ion exchange chromatography.
$^1$NMR Preparation of Intermediate D-5
1-(Boc-D,L-2-methylthiazol-4-ylglycinyl)-4-[(1-piperidinyl)methyl]piperidine This was prepared by coupling N-Boc-D,L-(2-methylthiazol-4-ylglycine and 4-(1-piperidinylmethyl)piperidine as described above in the corresponding step in the preparation of Intermediate D-3.

Intermediate D-5
1-(D,L-2-Methylthiazol-4-ylglycinyl)-4-[(piperidin-1-yl)methyl]piperidine This was prepared by deprotection of 1-(Boc-D,L-2-methylthiazol-4-ylglycinyl)-4-[(piperidin-1-yl)methyl]-piperidine as above in the corresponding step in the preparation of Intermediate D-3.
$^1$NMR Preparation of Intermediate D-6
1-Boc-4-[(2,3,5,6-tetrachloropyrid-4-ylamino)methyl]-piperidine A mixture of 1-Boc-4-(aminomethyl)piperidine (2.0 g, 9.33 mmol), pentachloropyridine (2.58 g, 10.3 mmol) and potassium carbonate (2.58 g, 18.7 mmol) was heated at 60° C. in DMF (22 mL) for 2 h. Excess DMF was removed in vacuo and the residue taken in to water/ethyl acetate. The aqueous solution was extracted with ethyl acetate (×3) and the combined organic solution dried (MgSO$_4$) and concentrated in vacuo. Flash chromatography (SiO$_2$, hexane/diethyl ether 30% to 60% gave the product as a white solid (2.5 g, 62%).
$^1$NMR 1-Boc-4-[(pyrid-4-ylamino)methyl]piperidine To a stirred solution of 1-Boc-4-[(2,3,5,6-tetrachloropyrid-4-ylamino)methyl]piperidine (2.5 g, 5.83 mmol) in a mixture of methanol (23 mL) and THF (23 mL) was added sodium methoxide (1.89 g, 35 mmol) and 5% palladium on carbon (1.24 g). The mixture was hydrogenated for 30 h and the catayalst was filtered off and the solution concentrated in vacuo. The residue was taken up in ethyl acetate and washed with water and satd sodium bicarbonate. The aqueous washes were back extracted with ethyl acetate, and the combined organics dried (MgSO$_4$) and concentrated in vacuo to give the product (1.0 g, 59%).
$^1$NMR 4-[(Pyrid-4-ylamino)methyl]piperidine Dihydrochloride To a stirred solution of 1-Boc-4-[(pyrid-4-ylamino)methyl]piperidine (1.0 g, 3.43 mmol) in methanol (100 mL) was added HCl (1 M in ether, 34 mL), and the mixture stirred overnight. The solvent was removed in vacuo, and the resudue taken up in water and freeze dried to give the product as a yellow solid (800 mg, 88%).

1-(Boc-D-phenylglycinyl)-4-[(pyrid-4-ylamino)methyl] piperidine Trifluoracetic Acid Salt To a mixture of Boc-D-phenylglycine (276 mg, 1.1 mmol), 4-[(pyrid-4-ylamino)methyl]piperidine dihydrochloride (290 mg, 1.1 mmol), HOAT (165 mg, 1.21 mmol) and triethylamine (367 mg, 3.63 mmol) in DMF (9 mL) was added EDCI (232 mg, 1.21 mmol), and the mixture stirred for 7 h at ambient temperature and 64 h at 5° C. The solvent was removed in vacuo and the residue partitioned between dilute aqueous sodium bicarbonate and 2:1 chloroform:isopropanol. The aqueous solution was back extracted with 2:1 chloroform:isopropanol three times and the combined extracts dried (MgSO$_4$). The solvent was removed in vacuo, and the crude product purified by RPHPLC to give product (500 mg) as a TFA salt.

Intermediate D-6
1-(D-Phenylglycinyl)-4-[(pyrid-4-ylamino)methyl] piperidine

To 1-(Boc-D-phenylglycinyl)-4-[(pyrid-4-ylamino) methyl]piperidine TFA salt (500 mL, 1.1 mmol) dissolved in DCM (9 mL) and anisole (1.79 mL, 16.5 mmol) was added TFA (2.3 mL), and the mixture stirred for 3 h. The solvent was removed in vacuo, and the residue purified by SCX ion exchange chromatography to give the product (290 mg, 81% over two steps).

PREPARATION OF EXAMPLES 1–5

General Procedure

Unless otherwise indicated, the product of Examples 1–5 was obtained from the indicated amine and 1-(4-methoxybenzoyl-D-phenylglycinyl)piperidine-4-carboxaldehyde (Intermediate B-1) using Alkylation Method A.

Example 1

1-[(4-Methoxybenzoyl-D-phenylglycinyl)]-4-[(isopropylamino)methyl]piperidine Hydrochloride 1-(4-Methoxybenzoyl-D-phenylglycinyl)piperidine-4-carboxaldehyde (0.050 g, 0.131 mmol) and isopropylamine afforded, after treatment of the isolated product with excess hydrochloric acid in methanol and concentration, 37 mg of the title compound as a hydrochloride salt.
$^1$NMR
IS-MS, m/e 424 (M+1)

Example 2

1-(4-Methoxybenzoyl-D-phenylglycinyl)-4-[(dimethylamino)methyl]piperidine 1-(4-Methoxybenzoyl-D-phenylglycinyl)piperidine-4-carboxaldehyde (0.050 g, 0.131 mmol) and dimethylamine afforded 25 mg (47%) of the title compound.
1NMR
IS-MS, m/e 410 (M+1)

Example 3

1-[(4-Methoxybenzoyl-D-phenylglycinyl)]-4-[(N,N-diethylamino)methyl]piperidine Hydrochloride.

1-(4-Methoxybenzoyl-D-phenylglycinyl)piperidine-4-carboxaldehyde (0.050 g, 0.131 mmol) and diethylamine afforded, after treatment of isolated product with excess hydrochloric acid in methanol and concentration, 42 mg of the title compound as a hydrochloride salt.
$^1$NMR
IS-MS, m/e 438 (M+1)

Example 4

1-[(4-Methoxybenzoyl-D-phenylglycinyl)]-4-[(1-pyrrolidinyl)methyl]piperidine 1-(4-Methoxybenzoyl-D-phenylglycinyl)piperidine-4-carboxaldehyde (0.050 g, 0.131 mmol) and pyrrolidine afforded 27 mg (47%) of the title compound.
$^1$NMR
IS-MS, m/e 436 (M+1)

Example 5
1-[(4-Methoxybenzoyl-D-phenylglycinyl)]-4-[(3-pyrrolin-1-yl)methyl]piperidine Hydrochloride 1-(4-Methoxybenzoyl-D-phenylglycinyl)piperidine-4-carboxaldehyde (0.050 g, 0.131 mmol) and 3-pyrroline afforded, after treatment of isolated product with excess hydrochloric acid in methanol and concentration, 43 mg of the title compound as a hydrochloride salt.
$^1$NMR
IS-MS, m/e 434 (M+1)

PREPARATION OF EXAMPLES 6–18
General Procedure

Unless otherwise indicated, the product of Examples 6–18 was obtained from the indicated amine and 1-(indole-6-carbonyl-D-phenylglycinyl)-4-(methylsulfonyloxymethyl)piperidine (Intermediate C-2) or 1-(3-chloroindole-6-carbonyl-D-phenylglycinyl)-4-(methylsulfonyloxymethyl)piperidine (Intermediate C-3) using a procedure similar to that described in Example 6.

Where indicated, free bases were obtained by using SCX ion exchange chromatography; hydrochloride salts were obtained by dissolving the free base in ethyl acetate, treating with 1 M HCl in ether, removing the solvent in vacuc, redissolving the resulting HCl salt in water/acetonitrile and lyophilising.

Example 6
1-(Indole-6-carbonyl-D-phenylglycinyl)-4-[(isopropylamino)methyl]piperidine Trifluoroacetate Salt A solution of 1-(indole-6-carbonyl-D-phenylglycinyl)-4-(methylsulfonyloxymethyl)piperidine (100 mg, 0.213 mmol) and isopropylamine (0.18 mL, 2.1 mmol) in 1 mL of THF was treated with potassium carbonate (60 mg) and sodium iodide (32 mg, 0.21 mmol), and the mixture was heated at reflux. After 16 h, the mixture was concentrated and the residue purified by rpHPLC chromatography affording 24 mg (21%) of the title compound as a trifluoroacetate salt.
$^1$NMR
IS-MS, m/e 433 (M+1).

Example 6a
1-(Indole-6-carbonyl-D-phenylglycinyl)-4-[(isopropylamino)methyl]piperidine Hydrochloride Salt The trifluoroacetate salt was converted to the hydrochloride salt via the free base as described above.
ES-MS, m/e 433 (M+1).

Example 7
1-(Indole-6-carbonyl-D-phenylglycinyl)-4-[4-(pyrrolidin-1-yl)methyl]piperidine Trifluoroacetate Salt Intermediate C-2 (200 mg, 0.426 mmol) and pyrrolidine (0.85 mmol) afforded, after purification by rpHPLC chromatography, 38 mg (16%) of the title compound as a trifluoroacetate salt.
$^1$NMR

Example 7a
1-(Indole-6-carbonyl-D-phenylglycinyl)-4-[4-(pyrrolidin-1-yl)methyl]piperidine Hydrochloride Salt The trifluoroacetate salt was converted to the hydrochloride salt via the free base as described above.
ES-MS, m/e 445 (M+1).

Example 8
1-(Indole-6-carbonyl-D-phenylglycinyl)-4-[(diethylamino)methyl]piperidine Trifluoroacetate Salt Intermediate C-2 (100 mg, 0.213 mmol) and diethylamine (2.1 mmol) afforded, after purification by rpHPLC chromatography, 59 mg (49%) of the title compound as a trifluoroacetate salt.
1NMR
IS-MS, m/e 447 (M+1)

Example 8a
1-(Indole-6-carbonyl-D-phenylglycinyl)-4-[(diethylamino)methyl]piperidine Hydrochloride salt The trifluoroacetate salt was converted to the hydrochloride salt via the free base as described above.
ES-MS, m/e 447 (M+1).

Example 9
1-(Indole-6-carbonyl-D-phenylglycinyl)-4-[(piperidin-1-yl)methyl]piperidine Trifluoroacetate Salt Intermediate C-2 (100 mg, 0.213 mmol) and piperidine (2.3 mmol) afforded, after purification by rpHPLC chromatography, 16 mg (13%) of the title compound as a trifluoroacetate salt.
$^1$NMR
IS-MS, m/e 459 (M+1).

Example 9a
1-(Indole-6-carbonyl-D-phenylglycinyl)-4-(piperidin-1-yl)methyl]piperidine Hydrochloride Salt The trifluoroacetate salt was converted to the hydrochloride salt via the free base as described above.
ES-MS, m/e 449 (M+1).

Example 10
1-(Indole-6-carbonyl-D-phenylglycinyl)-4-[(4-hydroxypiperidin-1-yl)methyl]piperidine Trifluoroacetate Salt Intermediate C-2 (100 mg, 0.213 mmol) and 4-hydroxypiperidine (2.3 mmol) afforded, after purification by rpHPLC chromatography, 32 mg (25%) of the title compound as a trifluoroacetate salt.
$^1$NMR
IS-MS, m/e 475 (M+1).

Example 10a
1-(Indole-6-carbonyl-D-phenylglycinyl)-4-[(4-hydroxypiperidin-1-yl)methyl]piperidine Hydrochloride Salt The trifluoroacetate salt was converted to the hydrochloride salt via the free base as described above.
ES-MS, m/e 475 (M+1)

Example 11
1-(Indole-6-carbonyl-D-phenylglycinyl)-4-[(piperazin-1-yl)methyl]piperidine Trifluoroacetate Salt Intermediate C-2 (100 mg, 0.213 mmol) and piperazine (2.3 mmol) afforded, after purification by rpHPLC chromatography, 85 mg (70%) of the title compound as a trifluoroacetate salt.
$^1$NMR
IS-MS, m/e 460 (M+1).

Example 12
1-(Indole-6-carbonyl-D-phenylglycinyl)-4-[(4-methylpiperazin-1-yl)methyl]piperidine Trifluoroacetate Salt Intermediate C-2 (100 mg, 0.213 mmol) and 1-methylpiperizine (2.3 mmol) afforded, after purification by rpHPLC chromatography, 66 mg (53%) of the title compound as a trifluoroacetate salt.
$^1$NMR
IS-MS, m/e 474 (M+1).

Example 13
1-(Indole-6-carbonyl-D-phenylglycinyl)-4-[(3-hydroxypyrrolidin-1-yl)methyl]piperidine Trifluoroacetate Salt Intermediate C-2 (100 mg, 0.213 mmol) and 3-hydroxypyrrolidine (2.3 mmol) afforded, after purification by rpHPLC chromatography, 36 mg (30%) of the title compound as a trifluoroacetate salt.
$^1$NMR
IS-MS, m/e 461 (M+1).

Example 16
1-(Indole-6-carbonyl-D-phenylglycinyl)-4-[(4-hydroxymethylpiperidin-1-yl)methyl]piperidine Trifluoroacetate Salt Intermediate C-2 (100 mg, 0.213 mmol) and 4-hydroxymethylpiperidine (2.3 mmol) afforded, after purification by rpHPLC chromatography, 28 mg (22%) of the title compound as a trifluoroacetate salt.
$^1$NMR
IS-MS, m/e 489 (M+1).

Example 17
1-(3-Chloroindole-6-carbonyl-D-phenylglycinyl)-4-[(piperidin-1-yl)methyl]piperidine Hydrochloride Salt Intermediate C-3 (1.0 g, 2.0 mmol) and piperidine (6.0 mmol) afforded, after purification by column chromatography (SiO$_2$: 2% to 4% [2 N ammonia in methanol]:methylene chloride) and salt formation with hydrochloric acid, 443 mg (41%) of the title compound as a hydrochloride salt.
$^1$NMR
IS-MS, m/e 493 (M+1)

Example 18
1-(3-Chloroindole-6-carbonyl-D-phenylglycinyl)-4-[(3-hydroxypiperidin-1-yl)methyl]piperidine.

Intermediate C-3 (1.50 g, 3.0 mmol) and 3-hydroxypiperidine (9.0 mmol) afforded, after purification by column chromatography (SiO$_2$: 2% to 3% [2 N ammonia in methanol]:methylene chloride), 1.10 g of the title compound.
$^1$NMR
IS-MS, m/e 507 (M+1).

Preparation of Examples 19–21
General Procedure

Unless otherwise indicated, the product of Examples 19–21 was obtained from the indicated carboxylic acid and 1-(D-phenylglycinyl)-4-[(piperidin-1-yl)methyl]piperidine (Intermediate D-1) using a procedure similar to that described in Example 19.

Example 19
1-(Indole-6-carbonyl-D-phenylglycinyl)-4-[(piperidin-1-yl)methyl]piperidine
Coupling Method B A solution of 1-(D-phenylglycinyl)-4-[(piperidin-1-yl)methyl]piperidine (4.00 g, 12.7 mmol) and indole-6-carboxylic acid (2.25 g, 13.9 mmol) in 60 mL of DMF was treated with HOBT (1.88 g, 13.9 mmol), the mixture cooled to 0° C., and then treated with DCC (2.87 g, 13.9 mmol). After 15 h, the mixture was diluted with EtOAc, filtered, and the filtrate concentrated. The residue was purified by column chromatography (SiO$_2$; 2% to 3.5% [2 N ammonia in methanol]:methylene chloride) to afford 3.1 g (53%) of the title compound.
$^1$NMR
IS-MS, m/e 459 (M+1).

Example 20
1-(3-Methylindole-6-carbonyl-D-phenylglycinyl)-4-[(piperidin-1-yl)methyl]piperidine Hydrochloride Salt Intermediate D-1 (2.00 g, 6.35 mmol) and 3-methylindole-6-carboxylic acid (1.22 g, 6.98 mmol) afforded, after formation of the hydrochloride salt, 1.29 g (41%) of the title compound.
$^1$NMR
IS-MS, m/e 473 (M+1).
Analysis for $C_{29}H_{36}N_4O_2 \cdot HCl \cdot 0.75\ H_2O$:
Calcd: C, 66.7; H, 7.4; N, 10.7;
Found: C, 66.7; H, 7.2; N, 10.8.

Example 21
1-(5-Chloroindole-2-carbonyl-D-phenylglycinyl)-4-[(piperidin-1-yl)methyl]piperidine Hydrochloride Salt Intermediate D-1 and 5-chloro-1H-indole-2-carboxylic acid (1.36 g, 6.98 mmol) afforded, after formation of the hydrochloride salt, 1.52 g (45%) of the title compound.
$^1$NMR
IS-MS, m/e 493 (M+1).
Analysis for $C_{28}H_{33}ClN_4O_2 \cdot HCl \cdot 0.75\ H_2O$:
Calcd: C, 61.9; H, 6.6; N, 10.3;
Found: C, 61.8; H, 6.4; N, 10.4.

Example 22
1-[4-Methoxybenzoyl-D,L-(2-methoxyphenyl)glycinyl]-4-[(piperidin-1-yl)methyl]piperidine hydrochloride Using Coupling Method B, 4-methoxybenzoic acid (0.29 g, 1.89 mmol) and 1-[D,L-(2-methoxyphenyl)glycinyl]-4-[(piperidin-1-yl)methyl]piperidine (0.59 g, 1.7 mmol) afforded, after purification by column chromatography (SiO$_2$; 0–4% [2 N ammonia in methanol]:methylene chloride), 0.47 g of 1-[4-methoxybenzoyl-D,L-(2-methoxyphenyl)glycinyl]-4-[(piperidin-1-yl)methyl]piperidine. The free base was dissolved in methylene chloride, and 1 M HCl in diethyl ether (1 mL, 1 mmol) was added with stirring. The mixture was partially concentrated and filtered to give 0.34 g (39%) of the title compound followed by a second crop of 0.12 g (14%).
$^1$NMR
IS-MS, m/e 480.1 (M+1)
Analysis for $C_{28}H_{37}N_3O_4 \cdot 0.95\ HCl \cdot 1.0\ H_2O$
Calcd: C, 63.18; H, 7.57; N, 7.90; Cl, 6.33;
Found: C, 63.43; H, 7.41; N, 7.68; Cl, 5.93.

Example 23
1-[Indole-6-carbonyl-D,L-(2-methoxyphenyl)glycinyl]-4-[(piperidin1-yl)methyl]piperidine hydrochloride Using Coupling Method B, indole-6-carboxylic acid (0.29 g, 1.89 mmol) and 1-[D,L-(2-methoxyphenyl)glycinyl]-4-[(piperidin-1-yl)methyl]piperidine (0.59 g, 1.7 mmol) afforded, after purification by column chromatography (SiO$_2$; 0–4% [2 N ammonia in methanol]:methylene chloride), 0.36 g of 1-[indole-6-carbonyl-D,L-(2-methoxyphenyl)glycinyl]-4-[(piperidin-1-yl)methyl] piperidine. The free base was dissolved in methylene chloride, and 1 M HCl in diethyl ether (1 mL, 1 mmol) was added with stirring. The mixture was partially concentrated and filtered to give 0.21 g (24%) of the title compound followed by a second crop of 0.065 g (7%).
$^1$NMR
IS-MS, m/e 489.0 (M+1)
Analysis for $C_{29}H_{36}N_4O_3 \cdot 1.0HCl \cdot 1.5H_2O$
Calcd: C, 63.09; H, 7.30; N, 10.15; Cl, 6.42;
Found: C, 62.99; H, 7.06; N, 9.90; Cl, 6.27.

Example 24
1-(4-Methoxybenzoyl-D,L-thiazol-5-ylglycinyl)-4-[(piperidin-1-yl)methyl]piperidine Hydrochloride Salt To a stirred solution of 4-methoxybenzoic acid (797 mg, 5.24 mmol), 1-(D,L-thiazol-5-ylglycinyl)-4-[(piperidin-1-yl-methyl]piperidine (circa 5.24 mmol) and HOAT (786 mg, 5.76 mmol) in DMF (40 mL) was added EDCI (1.11 g, 5.76 mmol). The mixture was stirred at room temperature for 20 h and the solvent removed in vacuo. The residues taken up in chloroform: isopropyl alcohol (2:1) and washed with satd sodium bicarbonate. The aqueous phase was back extracted with chloroform: isopropyl alcohol (2:1) (×3), and the combined organic extracts were dried (MgSO$_4$) and concentrated in vacuo. Half of the crude product was purified by preparative RPHPLC; and the product fractions concentrated, taken up in chloroform: isopropyl alcohol (2:1), washed with satd sodium bicarbonate, dried (MgSO$_4$) and concentrated in vacuo. The free base thus obtained was dissolved in methanol and treated with 2 equivalents of HCl in ether and evaporated to dryness. The residue was dissolved in water/acetonitrile and freeze dried. Yield 672 mg.
$^1$NMR
LCMS, m/e 457 (M+1)

Example 25
1-(4-Methoxybenzoyl-D,L-2-aminothiazol-4-ylglycinyl)-4-[(piperidin-1-yl)methyl]piperidine Hydrochloride Salt The title compound was prepared by the coupling of 1-(D,L-2-aminothiazol-4-ylglycinyl)-4-[(piperidin-1-yl)methylpiperidine and 4-methoxybenzoic acid using a procedure similar to that described in Example 24.
$^1$NMR
LCMS, m/e 472 (M+1)

Example 26
1-(4-Methoxybenzoyl-D,L-2-methylthiazol-4-ylglycinyl)-4-[(piperidin-1-yl)methyl]piperidine Hydrochloride Salt The title compound was prepared by the coupling of 1-(D,L-2-methylthiazol-4-ylglycinyl)-4-[(piperidin-1-yl-methyl)piperidine and 4-methoxybenzoic acid using a procedure similar to that described in Example 24.
$^1$NMR
LCMS, m/e 471 (M+1)

Example 27
1-(3-Chloroindole-6-carbonyl-D-phenylglycinyl)-4-[(cyclohexylamino)methyl]piperidine Hydrochloride
A. 1-(1-Methylsulfonyl-3-chloroindole-6-carbonyl-D-phenylglycinyl)-4-[(cyclohexylamino)methyl]piperidine Using a procedure similar to that described above for Example 6, 1-(1-methylsulfonyl-3-chloroindole-6-carbonyl-D-phenylglycinyl)-4-(methylsulfonyloxymethyl)piperidine (940 mg, 1.6 mmol) and cyclohexylamine (1.3 mL, 11.2 mmol) afforded, after purification by column chromatography (SiO$_2$: 2% 2 N ammonia in methanol:methylene chloride), 600 mg (63%) of the title compound.
$^1$NMR
IS-MS, m/e 585 (M+1)

B. 1-(3-Chloroindole-6-carbonyl-D-phenylglycinyl)-4-](cyclohexylamino)methyl]piperidine Hydrochloride To a solution of 1-(1-methylsulfonyl-3-chloroindole-6-carbonyl-D-phenylglycinyl)-4-[(cyclohexylamino)methyl]piperidine (100 mg, 0.17 mmol) in 4 mL of methanol was added potassium hydroxide (50 mg, 0.89 mmol). After stirring for 1 h, filtration of the resultant white precipitate afforded 35 mg (40%) of the title compound.
$^1$NMR
IS-MS, m/e 507 (M+1)

The free base was converted into the hydrochloride salt.
Alternatively, using the method described above for Example 6, reaction of Intermediate C-3 and cyclohexylamine affords, after purification and conversion to the hydrochloride salt, the title compound.

Example 28
1-(Indole-6-carbonyl-D-phenylglycinyl)-4-[(pyrid-4-ylamino)methyl]piperidine To a solution of indole-6-carboxylic acid (144 mg, 0.894 mmol), 1-(D-phenylglycinyl)-4-[(pyrid-4-ylamino)methyl]piperidine (290 mg, 0.894 mg) and HOAT (134 mg, 0.983 mmol) in DMF (7 mL) was added EDCI (189 mg, 0.983 mmol) and the mixture stirred for 5 h at ambient temperature and 18 h at 5° C. The DMF was removed in vacuo and the residue purified by RPHPLC. The TFA salt obtained was converted to the free base by dissolving in 2:1 chloroform:isopropanol and washing with aqueous sodium bicarbonate, drying (MgSO$_4$) and evaporating solvent in vacuo to give the title compound (325 mg, 78%).
$^1$NMR The following compounds are prepared using similar procedures to those described above and the requisite starting materials:

1-[Indole-6-carbonyl-D,L-(5-thiazoyl)glycinyl]-4-[(piperidin-1-yl)methyl]piperidine
1-[Indole-6-carbonyl-D,L-(2-aminothiazol-4-yl)glycinyl]-4-[(piperidin-1-yl)methyl]piperidine
1-[Indole-6-carbonyl-D,L-(2-methylthiazol-4-yl)glycinyl]-4-[(piperidin1-yl)methyl]piperidine
1-[3-Methylindole-6-carbonyl-D,L-(4-pyridyl)glycinyl]-4-[(piperidin-1-yl)methyl]piperidine
1-[3-Chloroindole-6-carbonyl-D,L-(4-pyridyl)glycinyl]-4-[(piperidin-1-yl)methyl]piperidine
1-[3-Methylindole-6-carbonyl-D,L-(2-methoxyphenyl)glycinyl]-4-[(piperidin1-yl)methyl]piperidine
1-[3-Chloroindole-6-carbonyl-D,L-(2-methoxyphenyl)glycinyl]-4-[(piperidin1-yl)methyl]piperidine
1-[Indole-6-carbonyl-D,L-(1-naphthyl)glycinyl]-4-[(piperidin-1-yl)methyl]piperidine
1-[3-Methylindole-6-carbonyl-D,L-(1-naphthyl)glycinyl]-4-[(piperidin1-yl)methyl]piperidine
1-[3-Chloroindole-6-carbonyl-D,L-(1-naphthyl)glycinyl]-4-[(piperidin1-yl)methyl]piperidine
1- [Indole-6-carbonyl-D,L-(2-chlorophenyl)glycinyl]-4-[(piperidin-1-yl)methyl]piperidine
1-[3-Methylindole-6-carbonyl-D,L-(2-chlorophenyl)glycinyl]-4-[(piperidin1-yl)methyl]piperidine
1-[3-Chloroindole-6-carbonyl-D,L-(2-chlorophenyl)glycinyl]-4-[(piperidin1-yl)methyl]piperidine
1-[Indole-6-carbonyl-D,L-(8-quinolinyl)glycinyl]-4-[(piperidin-1-yl)methyl)piperidine
1-[3-Methylindole-6-carbonyl-D,L-(8-quinolinyl)glycinyl]-4-[(piperidin1-yl)methyl]piperidine
1-[3-Chloroindole-6-carbonyl-D,L-(8-quinolinyl)glycinyl]-4-[(piperidin1-yl)methyl]piperidine
1-[Indole-6-carbonyl-D,L-(4-quinolinyl)glycinyl]-4-[(piperidin-1-yl)methyl]piperidine 1-[3-Methylindole-6-carbonyl-D,L-(4-quinolinyl)glycinyl]-4-[(piperidin1-yl)methyl]piperidine 1-[3-Chloroindole-6-carbonyl-D,L-(4-quinolinyl)glycinyl]-4-[(piperidin-1-yl)methyl]piperidine 1-(Indole-6-carbonyl-D-phenylglycinyl)-4-((R)-(3-hydroxy-methylpyrrolidin-1-yl) methyl]piperidine Trifluoroacetate Salt 1-(Indole-6-carbonyl-D-phenylglycinyl)-4[-(R)-(3-hydroxy-methylpyrrolidin-1-yl) methyl]piperidine Hydrochloride Salt 1-(Indole-6-carbonyl-D-phenylglycinyl)-4-[(S)-(3-hydroxymethylpyrrolidin-1-yl) methyl]piperidine Trifluoroacetate Salt Assay Protocols Enzyme Inhibition Assays The ability of a test compound to inhibit factor Xa may be evaluated in one or more of the following Enzyme Inhibition assays, or in other standard assays known to those skilled in the art.

Enzyme Inhibition Assay 1

Enzyme assays were carried out at room temperature in 0.1M phosphate buffer, pH7.4 according to the method of Tapparelli et al (J. Biol. Chem. 1993,268,4734–4741). Purified human factor Xa, trypsin, thrombin and plasmin were purchased from Alexis Corporation, Nottingham, UK. Urokinase was purchased from Calbiochem, Nottingham, UK. Chromogenic substrates for these enzymes; pefachrome-FXA, pefachrome-TRY, pefachrome-TH, pefachrome-PL and pefachrome-UK were purchased from Pentapharm G, Basel, Switzerland. Product (p-nitroaniline) was quantified by adsorption at 405 nm in 96 well microplates using a Dynatech MR5000 reader (Dynex Ltd, Billingshurst, UK). Km and Ki were calculated using SAS PROC NLIN (SAS Institute, Cary, N.C., USA, Release 6.11) $K_m$ values were determined as 100.9 $\mu$M for factor Xa/pefachrome-FXA and 81.6 $\mu$M for trypsin/pefachrome-TRY. Inhibitor stock solutions were prepared at 40 mM in Me2SO and tested at 500 $\mu$M, 50 $\mu$M and 5 $\mu$M. Accuracy of Ki measurements was confirmed by comparison with Ki values of known inhibitors of factor Xa and trypsin.

In agreement with published data, benzamidine inhibited factor Xa, trypsin, thrombin, plasmin and urokinase with Ki values of 155 $\mu$M, 21 $\mu$M, 330 nM, 200 nM and 100 nM respectively. NAPAP inhibited thrombin with a Ki value of 3 nM. Compounds of the invention were found to have activity in these assays.

Enzyme Inhibition Assay 2

Human factor Xa and human thrombin were purchased from Enzyme Research Laboratories (South Bend, Ind., USA). Other proteases were from other commercial sources. Chromogenic para-nitroanilide peptide protease substrates were purchased from Midwest Biotech (Fishers, Ind., USA).

The binding affinities for human factor Xa were measured as apparent association constants (Kass) derived from protease inhibition kinetics as described previously.[a,b,c,d] The apparent Kass values were obtained using automated (BioMek-1000) dilutions of inhibitors (Kass determinations are performed in triplicate at each of four-eight inhibitor concentrations) into 96-well plates and chromogenic substrate hydrolysis rates determined at 405 nm using a Thermomax plate reader from Molecular Devices (San Francisco). For factor Xa inhibition, the assay protocol was: 50 $\mu$l buffer (0.06 M tris, 0.3 M NaCl, pH 7.4); 25 $\mu$l inhibitor test solution (in MeOH); 25 $\mu$l human factor Xa (32 nM in 0.03 M tris, 0.15 M NaCl, 1 mg/ml HSA); finally, 150 $\mu$l BzIleGluGlyArgpNA (0.3 mM in water) added within 2 min to start hydrolysis. Final factor Xa was 3.2 nM. Free [Xa] and bound [Xa] were determined from linear standard curves on the same plate by use of SoftmaxPro software for each inhibitor concentration and apparent Kass calculated for each inhibitor concentration which produced hydrolysis inhibition between 20% and 80% of the control (3.2 nM factor Xa): apparent Kass=$[E:I]/[E_f][I_f]=[E_b]/[E_f][I^o-I_b]$. The apparent Kass values so obtained are approximately the inverse of the Ki for the respective inhibitors [1/appKass= app Ki]. The variability of mean apparent Kass values determined at the single substrate concentration was +/−15%. The assay system Km was measured as 0.347+/−0.031 mM [n=4]; and Vmax was 13.11+/−0.76 $\mu$M/min.

Kass values were determined with thrombin and other proteases using the same protocol with the following enzyme and substrate concentrations: thrombin 5.9 nM with 0.2 mM BzPheValArgpNA; XIa 1.2 nM with 0.4 mM pyroGluProArgpNA; XIIa 10 nM with 0.2 mM HDProPheArgpNA; plasmin 3.4 nM with 0.5 mM HDValLeu-LyspNA; nt-PA 1.2 nM with 0.8 mM HDIleProArgpNA; and urokinase 0.4 nM with 0.4 mM pyroGluGlyArgpNA; aPC 3 nM with 0.174 mM pyroGluProArgpNA; plasma kallikrein 1.9 nM with D-ProPheArgpNA; bovine trypsin 1.4 nM with 0.18 mM BzPheValArgpNA.

Citations (a) Sall D J, J A Bastian, S L Briggs, J A Buben, N Y Chirgadze, D K Clawson, M L Denny, D D Giera, D S Gifford-Moore, R W Harper, K L Hauser, V J Klimkowski, T J Kohn, H-S Lin, J R McCowan, A D Palkowitz, G F Smith, M E Richett, K Takeuchi, K J Thrasher, J M Tinsley, B G Utterback, S-CB Yan, M Zhang. Dibasic Benzo[b]thiophenes Derivatives as a Novel Class of Active Site Directed Thrombin Inhibitors. 1. Determination of the Serine Protease Selectivity, Structure-Activity Relationships and Binding Orientation. J Med Chem 40 3489–3493 (1997).

(b) Smith G F, T J Craft, D S Gifford-Moore, W J Coffman, K D Kurz, E Roberts, R T Shuman, G E Sandusky, N D Jones, N Chirgadze, and C V Jackson. A Family of Arginal Thrombin Inhibitors Related to Efegatran. Sem. Thrombos. Hemost. 22, 173–183 (1996).

(c) Smith G F, D S Gifford-Moore, T J Craft, N Chirgadze, K J Ruterbories, T D Lindstrom, J H Satterwhite. Efegatran: A New Cardiovascular Anticoagulant. In New Anticoagulants for the Cardiovascular Patient. Ed. R Pifarre. Hanley & Belfus, Inc., Philadelphia (1997) pp 265–300.

(d) Sall D J, J A Bastian, N Y Chirgadze, M L Denny, M J Fisher, D S Gifford-Moore, R W Harper, V J Klimkowski, T J Kohn, H S Lin, J R McCowan, M E Richett, G F Smith, K Takeuchi, J E Toth, M Zhang. Diamino Benzo[b]thiophene Derivatives as a Novel C1 ass of Active Site Directed Thrombin Inhibitors: 5. Potency, Efficacy and Pharmacokinetic Properties of Modified C-3 Side Chain Derivatives. In press, J Med Chem (1999).

In general, the compounds of formula (I) exemplified herein have been found to exhibit a Ki of 10 $\mu$M or less in Assay 1 and/or a Kass of at least 0.1×10$^6$ L/mole in Assay 2.

The ability of a test compound to elongate Partial Thromboplastin Time (Prothrombin Time) may be evaluated in the following test protocols.

Partial Thromboplastin Time (Prothrombin) Test Protocol

Venous blood was collected into 3.2% (0.109 m) trisodium citrate vacutainer tubes at 1 volume of anticoagulant to nine volumes of blood. The blood cells were separated by centrifugation at 700 g for ten minutes to yield plasma, which was frozen at 70° C. until required.

To perform the test 100 $\mu$l of plasma was pipetted into in a glass test tube, 1 $\mu$l of test compound in DMSO was added, and allowed to warm to 37° over two minutes. 100 µl of warm (370°) Manchester (tissue thromboplasin) reagent (Helena Biosciences, UK) was added, allowed to equilibrate for two minutes. 100 µl of warm (37°) 25 mM calcium chloride solution was added to initiate clotting. The test tube was tilted three times through a 90° angle every five seconds to mix the reagents and the time to clot formation recorded. Data from a series of observations and test compound concentrations are analysed by a SAS statistical analysis program and a CT2 (Concentration required to double clotting time) for each compound is generated.

Compounds of the invention were found to significantly elongate the partial thromboplastin time (Prothrombin time).

Alternative Prothrombin Time and APTT Protocols

Coagulation Determinations. Prothrombin Times and APTT values were determined in HUMAN PLASMA with a STA instrument (Stago). BioPT is a special non-plasma clotting assay triggered with human tissue factor (Innovin). Possible binding to albumen or to lipid was assessed by comparing the BioPT effects in the presence/absence of 30 mg/ml human albumen (HSA) and 1 mg/ml phosphatidyl choline (PC). Inhibitors were delivered in 50% MeOH vehicle.

APTT ASSAY

75 µl plasma Citrol Baxter-Dade Citrated Normal Human Plasma

25 µl test sol'n

75 µl Actin Baxter-Dade Activated Cephaloplastin incubate 2 min min. @ 37°

75 µl CaCl$_2$ (0.02 M)

PT ASSAY

75 µl plasma

25 µl test sol'n

75 µl saline incubate 1 min. @ 37° C.

75 µl Innovin Baxter-Dade Recombinant Human Tissue Factor

Compounds of the invention were found to be potent inhibitors of factor Xa.

What is claimed is:

1. A serine protease inhibitor compound of formula (I)

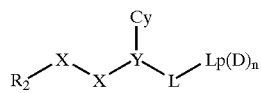

(I)

wherein:

R$_2$ is:
(i) phenyl optionally being substituted in the 3 and/or 4 position by halo, nitro, thiol, haloalkoxy, hydrazido, alkylhydrazido, amino, cyano, haloalkyl, alkylthio, alkenyl, alkynyl, acylamino, tri or difluoromethoxy, carboxy, acyloxy, MeSO$_2$— or R$_1$, and optionally substituted at the 6 position by amino, hydroxy, halo, alkyl, carboxy, alkoxycarbonyl, cyano, amido, aminoalkyl, alkoxy or alkylthio;
(ii) naphth-2-yl optionally substituted at the 6 or 7 position by halo, haloalkoxy, haloalkyl, cyano, nitro, amino, hydrazido, alkylthio, alkenyl, alkynyl or R$_{1j}$ and optionally substituted at the 3 position by amino, hydroxy, halo, alkyl, carboxy, cyano, amido, aminoalkyl, alkoxy or alkylthio;
(iii) isoquinolin-7-yl, indol-5-yl, indol-6-yl, indazol-5-yl, indazol-6-yl, benzothiazol-6-yl or benzisoxazol-5-yl optionally substituted at the 3 position by halo, haloalkoxy, haloalkyl, cyano, nitro, amino, hydrazido, alkylthio, alkenyl, alkynyl or R$_{1j}$;
(iv) benzimidazol-5-yl or benzothiazol-6-yl optionally substituted at the 2 position by amino;
(v) thien-2-yl or thien-3-yl optionally substituted at the 4 or 5 position by halo, haloalkoxy, haloalkyl, cyano, nitro, amino, hydrazido, alkylthio, alkenyl, alkynyl or R$_1$;
(vi) 3,4-methylenedioxyphenyl, 2,3-dihydroindol-6-yl, 3,3-dichloro-2-oxo-indol-6-yl or 1-methyl-3-aminoindazol-5-yl;
(vii) benzothiazol-2-yl, imidazo[1,2-a]pyrimidin-2-yl or tetrahydroimidazo[1,2-a]pyrimidin-2-yl;
(viii) pyrazol-2-yl optionally substituted at the 5 position by halo, haloalkoxy, haloalkyl, cyano, nitro, amino, hydrazido, alkylthio, alkenyl, alkynyl or R$_1$;
(ix) pyrid-2-yl optionally substituted at the 5 position by halo, haloalkoxy, haloalkyl, cyano, nitro, amino, hydrazido, alkylthio, alkenyl, alkynyl or R$_1$;
(x) pyrid-3-yl optionally substituted at the 6 position by halo, haloalkoxy, haloalkyl, cyano, nitro, amino, hydrazido, alkylthio, alkenyl, alkynyl or R$_1$;
(xi) benzofur-2-yl optionally substituted at the 3 position by amino, hydroxy, halo, alkyl, carboxy, cyano, amido, aminoalkyl, alkoxy or alkylthio and at the 5 or 6 position by halo, haloalkoxy, haloalkyl, cyano, nitro, amino, hydrazido, alkylthio, alkenyl, alkynyl or R$_{1j}$;
(xii) indol-2-yl optionally substituted on the indole nitrogen atom by alkyl and optionally substituted at the 5 or 6 position by halo, haloalkoxy, haloalkyl, cyano, nitro, amino, hydrazido, alkylthio, alkenyl, alkynyl or R$_{1j}$;
(xiii) indol-6-yl substituted at the 5 position by amino, hydroxy, halo, alkyl, carboxy, alkoxycarbonyl, cyano, amido, aminoalkyl, alkoxy or alkylthio and optionally substituted at the 3 position by halo, haloalkoxy, haloalkyl, cyano, nitro, amino, hydrazido, alkylthio, alkenyl, alkynyl or R$_{1j}$; or
(xiv) benzo[b]thiophen-2-yl optionally substituted at the 3 position by amino, hydroxy, halo, alkyl, carboxy, cyano, amido, aminoalkyl, alkoxy or alkylthio and at the 5 or 6 position by halo, haloalkoxy, haloalkyl, cyano, nitro, amino, hydrazido, alkylthio, alkenyl, alkynyl or R$_{1j}$;

with the proviso that R$_2$ cannot be aminoisoquinolyl;

R$_1$ is hydrogen; hydroxy; alkoxy; alkyl; alkylaminoalkyl; alkanoyl; hydroxyalkyl; alkoxyalkyl; alkoxycarbonyl; alkylaminocarbonyl; alkylamino; carboxyl; carboxymethyl; amido (CONH$_2$) or amidomethyl;

R$_{1j}$ is: hydrogen; hydroxy; alkoxy; alkyl; alkanol; hydroxyalkyl; alkoxyalkyl; alkoxycarbonyl; alkylamino; carboxyl; carboxymethyl; amido (CONH$_2$) or amidomethyl;

—X—X— is —CONH—;

Y (the α-atom) is CH;

Cy is an optionally R$_{3a}$ substituted: phenyl, pyridyl, thienyl, thiazolyl, naphthyl, piperidinyl, furanyl, pyrrolyl, isoxazolyl, isothiazolyl, pyrazolyl, oxazolyl, imidazolyl, 1,2,4-thiadiazolyl, 1,3,4-thiadiazolyl, pyrimidinyl, pyridazinyl, quinoloyl, isoquinolyl, benzofuryl, benzothienyl or cycloalkyl group, or a phenyl group substituted by R$_{3i}$x$_i$ in which x$_1$ is a bond, O, NH or CH$_2$ and R$_{3i}$ is phenyl, pyridyl or pyrimidinyl optionally substituted by R$_{3a}$;

each R$_{3a}$ independently is hydrogen; hydroxyl; alkoxy; alkyl; alkylaminoalkyl; hydroxymethyl; carboxy; alkoxyalkyl; alkoxycarbonyl; alkylaminocarbonyl;

aminomethyl; CONH₂; CH₂CONH₂; (1–6C) alkanoylamino; alkoxycarbonylamino; amino; halo; cyano; nitro; thiol; alkylthio; alkylsulphonyl; alkylsulphenyl; alkylsulphonamido; alkylaminosulphonyl; aminosulphonyl; haloalkoxy; haloalkyl; a group of the formula —C(X³)N(R¹¹)R¹² (wherein X³ is O or S and R¹¹ and R¹² are independently selected from hydrogen, methyl, ethyl, or together with the nitrogen atom to which they are attached form a pyrrolidin-1-yl, piperidin-1-yl or morpholino group; or —OCH₂O— which is bonded to two adjacent ring atoms in Cy and —L—Lp(D)$_n$ is

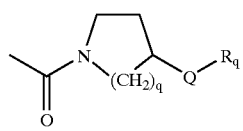

q is 1 or 2;

Q is methylene; and R$_q$ is NR$_a$R$_b$ in which each of R$_a$ and R$_b$ independently is hydrogen or C$_{1-3}$alkyl; or one of R$_a$ and R$_b$ is hydrogen or methyl and the other of R$_a$ and R$_b$ is (3–6C)cycloalkyl, pyrid-4-yl, —CH₂—R$_c$ or —CH₂—R$_d$ in which R$_c$ is pyridyl or phenyl (which phenyl may bear a fluoro, chloro, methyl, CONH₂, SO₂NH₂, methylaminosulphonyl, dimethylaminosulphonyl, methylsulphonylamino, methoxy or methylsulphonyl substituent) and in which R$_d$ is isopropyl or cyclopentyl, or NR$_a$R$_b$ is azetidino, pyrrolidino, piperidino, morpholino, thiomorpholino, piperazino, or tetrahydro-1,4-diazepino [in which a pyrrolidino or piperidino may be a 3,4-didehydro derivative and in which a azetidino, pyrrolidino, piperidino, morpholino, thiomorpholino, piperazino, or tetrahydro-1,4-diazepino may be optionally substituted on a ring carbon atom by hydroxy, amino, (1–3C) alkoxy, (1–3C)hydroxyalkyl, (1–3C)alkyl, carboxy, methoxycarbonyl or ethoxycarbonyl (provided that the amino, hydroxy or alkoxy substituent is not on a ring carbon atom which is included in a double bond, or adjacent to a ring oxygen, sulfur or nitrogen atom) and in which the piperazino or tetrahydro-1,4-diazepino may bear a methyl group at the 4-position];

or a physiologically-tolerable salt thereof.

2. A compound according to claim 1 wherein

Cy is an optionally R$_{3a}$ substituted: phenyl, pyridyl, thienyl, thiazolyl, naphthyl, piperidinyl or cycloalkyl group;

each R$_{3a}$ is selected from hydrogen, hydroxyl, methoxy, ethoxy, methyl, ethyl, methylaminomethyl, dimethylaminomethyl, hydroxymethyl, carboxy, methoxymethyl, methoxycarbonyl, ethoxycarbonyl, methylaminocarbonyl, dimethylaminocarbonyl, aminomethyl, CONH₂, CH₂CONH₂, acetylamino, methoxycarbonylamino, ethoxycarbonylamino, t-butoxycarbonylamino, amino, fluoro, chloro, cyano, nitro, thiol, methylthio, methylsulphonyl, ethylsulphonyl, methylsulphenyl, methylsulphonamido, ethylsulphonylamido, methylaminosulphonyl, ethylaminosulphonyl, aminosulphonyl, trifluoromethoxy and trifluoromethyl;

—L—Lp(D)$_n$ is of the formula:

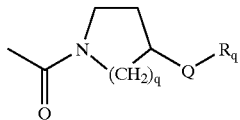

wherein:

q is 1 or 2;

Q is methylene; and R$_q$ is NR$_a$R$_b$ in which each of R$_a$ and R$_b$ independently is hydrogen or C$_{1-3}$alkyl; or one of R$_a$ and R$_b$ is hydrogen or methyl and the other of R$_a$ and R$_b$ is —CH₂—R$_c$ or —CH₂—R$_d$ in which R$_c$ is pyridyl or phenyl (which phenyl may bear a fluoro, chloro, methyl, CONH₂, SO₂NH₂, methylaminosulphonyl, dimethylaminosulphonyl, methylsulphonylamino, methoxy or methylsulphonyl substituent) and in which R$_d$ is isopropyl or cyclopentyl, or NR$_a$R$_b$ is pyrrolidino, piperidino, morpholino, piperazino, or tetrahydro-1,4-diazepino in which a pyrrolidino or piperidino may be a 3,4-didehydro derivative and in which a pyrrolidino, piperidino, piperazino, or tetrahydro-1,4-diazepino may bear a methyl group at the 4-position;

or a physiologically-tolerable salt thereof.

3. A compound according to claim 1 wherein q is 2.

4. A compound according to claim 1 wherein R$_q$ is NR$_a$R$_b$ in which R$_a$ is hydrogen or C$_{1-3}$alkyl and R$_b$ is C$_{1-3}$alkyl; or R$_a$ is hydrogen and R$_b$ is (3–6C)cycloalkyl or pyrid-4-yl; or NR$_a$R$_b$ is azetidino, pyrrolidino, piperidino, morpholino, thiomorpholino or piperazino [in which a pyrrolidino, piperidino or piperazino may be optionally substituted on a ring carbon atom by hydroxy or hydroxymethyl (provided that the hydroxy substituent is not on a ring carbon atom which is adjacent to a ring nitrogen atom) and in which the piperazino may bear a methyl group at the 4-position].

5. A compound according to claim 1 wherein R$_q$ is selected from dimethylamino, diethylamino, prop-2-ylamino, pyrrolidino, 3-pyrrolino, 3-hydroxypyrrolidino, 3-hydroxymethylpyrrolidino, piperidino, 3-hydroxypiperidino, 4-hydroxypiperidino, 4-hydroxymethylpiperidino, piperazino and 4-methylpiperazino.

6. A compound according to claim 1 wherein R₂ is selected from one of the formula (A') to (H'):

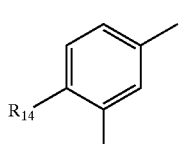
(A')

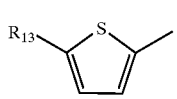
(B')

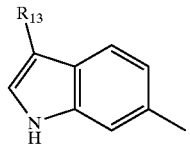
(C')

-continued (D')

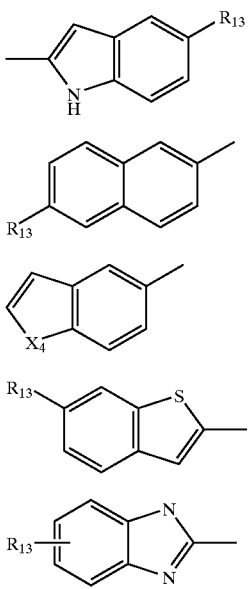

wherein $X_4$ is O or S, $R_{13}$ is selected from hydrogen, chloro or methyl and $R_{14}$ is selected from hydrogen, methyl, ethyl, fluoro, chloro, and methoxy and $R_{15}$ is selected from hydrogen, methyl, fluoro, chloro and amino.

7. A compound according to claim 6, wherein $R_2$ is 4-methoxyphenyl, 5-chloroindol-2-yl, 3-chloroindol-6-yl, indol-6-yl or 3-methylindol-6-yl.

8. A compound according to claim 1 wherein $R_{3a}$ is selected from hydrogen, hydroxyl, methoxy, ethoxy, methyl, ethyl, methylaminomethyl, dimethylaminomethyl, hydroxymethyl, carboxy, methoxymethyl, methoxycarbonyl, ethoxycarbonyl, methylaminocarbonyl, dimethylaminocarbonyl, aminomethyl, $CONH_2$, $CH_2CONH_2$, acetylamino, methoxycarbonylamino, ethoxycarbonylamino, t-butoxycarbonylamino, amino, fluoro, chloro, bromo, cyano, nitro, thiol, methylthio, methylsulphonyl, ethylsulphonyl, methylsulphenyl, methylsulphonylamido, ethylsulphonylamido, methylaminosulphonyl, ethylaminosulphonyl, aminosulphonyl, trifluoromethoxy, trifluoromethyl, pyrrolidin-1-ylcarbonyl, piperidin-1-ylcarbonyl or morpholin-1-ylcarbonyl and —OCH$_2$O— (which is bonded to two adjacent ring atoms in Cy).

9. A compound according to claim 1 wherein Cy is selected from:

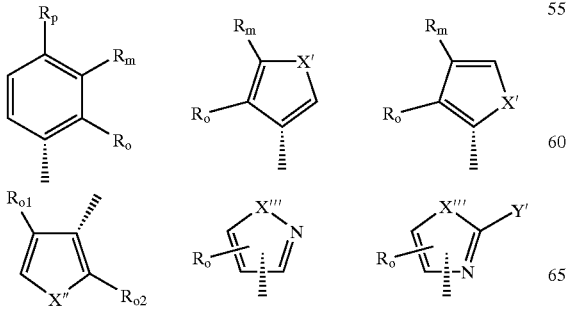

-continued

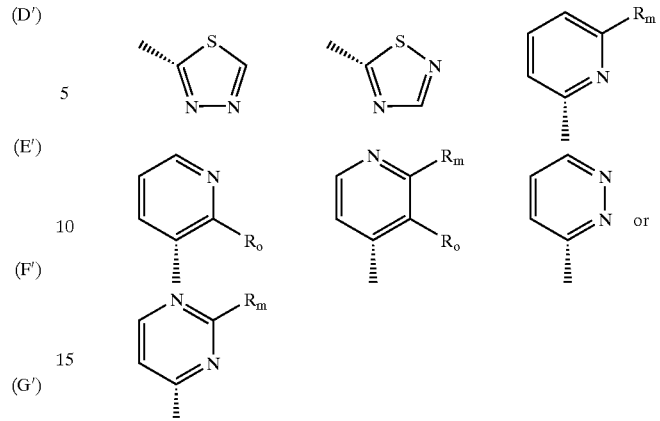

wherein:

X' is selected from O, S and NMe;

X" is selected from O and S;

X'" is selected from O, S, NH and NMe;

Y' is selected from hydrogen, amino and methyl;

$R_O$ is selected from hydrogen, methyl, fluoro, chloro, trifluoromethyl, methoxy, methylthio, methylsulphinyl and methylsulphonyl;

$R_m$ is selected from hydrogen, methyl, fluoro, chloro, trifluoromethyl, methoxy, methylthio, methylsulphinyl, methylsulphonyl, carboxy, methoxycarbonyl and a group of the formula —C(X$^3$)N(R$^{11}$)R$^{12}$ (wherein X$^3$ is O or S, and R$^{11}$ and R$^{12}$ are independently selected from hydrogen, methyl or ethyl or together with the nitrogen atom to which they are attached form a pyrrolidin-1-yl, piperidin-1-yl or morpholino group);

$R_p$ is selected from hydrogen and fluoro; or $R_o$ and $R_m$ or $R_m$ and $R_p$ form an —OCH$_2$O— group; or $R_o$ and $R_m$ together with the ring to which they are attached form a 5 or 6 membered aryl or heteroaryl ring (wherein the heteroary ring contains 1 or 2 heteroatoms selected from nitrogen, oxygen and sulfur); and one of $R_{o1}$ and $R_{o2}$ is hydrogen and the other is $R_o$.

10. A compound according to claim 9 wherein Cy is selected from phenyl, 2-chlorophenyl, 2-methoxyphenyl, 4-carbamoylphenyl, pyrid-2-yl, pyrid-4-yl, thien-2-yl, thien-3-yl, furan-2-yl, furan-3-yl, imidazol-2-yl, thiazol-2-yl, thiazol-4-yl, 2-amino-thiazol-4-yl, thiazol-5-yl, naphth-1-yl, isoquinolin-5-yl, isoquinolin-8-yl, quinolin-4-yl, quinolin-5-yl and quinolin-8-yl.

11. A compound as claimed in any one of claims 1 to 5, 6 to 7, 8 or 9 to 10, in which the alpha atom in Y has the conformation that would result from construction from a D-α-aminoacid NH$_2$—CH(Cy)—COOH where the NH$_2$ represents part of X—X.

12. A compound according to claim 1 wherein:

$R_2$ is selected from one of the formula (A') to (H'):

(A')

-continued

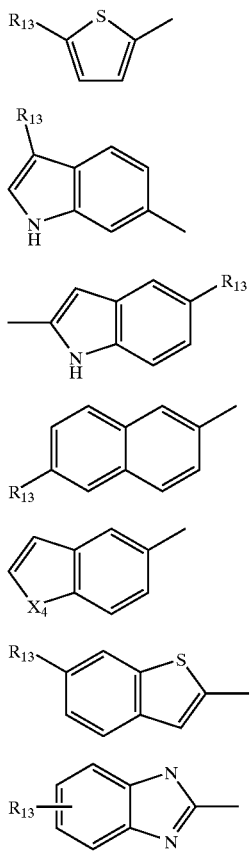

wherein $X_4$ is O or S, $R_{13}$ is selected from hydrogen, chloro or methyl and $R_{14}$ is selected from hydrogen, methyl, ethyl, fluoro, chloro, and methoxy and $R_{15}$ is selected from hydrogen, methyl, fluoro, chloro and amino;

—X—X— is —CONH—;

Y is CH and has the conformation that would result from construction from a D-α-aminoacid $NH_2$—CH(Cy)—COOH where the $NH_2$ represents past of X—X;

Cy is selected from

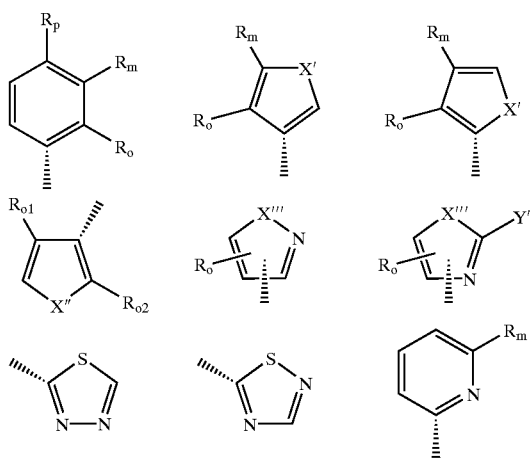

-continued

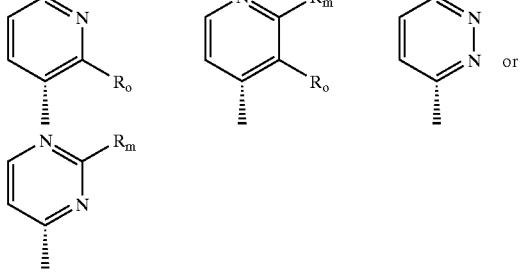

wherein:
- X' is selected from O, S and NMe;
- X" is selected from O and S;
- X'" is selected from O, S, NH and NMe;
- Y' is selected from hydrogen, amino and methyl;
- $R_o$ is selected from hydrogen, methyl, fluoro, chloro, trifluoromethyl, methoxy, methylthio, methylsulphinyl and methylsulphonyl;
- $R_m$ is selected from hydrogen, methyl, fluoro, chloro, trifluoromethyl, methoxy, methylthio, methylsulphinyl, methylsulphonyl, carboxy, methoxycarbonyl and a group of the formula —$C(X^3)N(R^{11})R^{12}$ (wherein $X^3$ is O or S, and $R^{11}$ and $R^{12}$ are independently selected from hydrogen, methyl or ethyl or together with the nitrogen atom to which they are attached form a pyrrolidin-1-yl, piperidin-1-yl or morpholino group);
- $R_p$ is selected from hydrogen and fluoro; or
- $R_o$ and $R_m$ or $R_m$ and $R_p$ form an —$OCH_2O$— group; or
- $R_o$ and $R_m$ together with the ring to which they are attached form a 5 or 6 membered aryl or heteroaryl ring (wherein the heteroary ring contains 1 or 2 heteroatoms selected from nitrogen, oxygen and sulfur); and
- one of $R_{o1}$ and $R_{o2}$ is hydrogen and the other is $R_o$; and q is 2.

13. A compound according to claim 12 wherein Rq is selected from dimethylamino, diethylamino, prop-2-ylamino, pyrrolidino, 3-pyrrolino, 3-hydroxypyrrolidino, 3-hydroxymethylpyrrolidino, piperidino, 3-hydroxypiperidino, 4-hydroxypiperidino, 4-hydroxymethylpiperidino, piperazino and 4-methylpiperazino.

14. A compound according to claim 13 wherein $R_2$ is 4-methoxyphenyl, 5-chloroindol-2-yl, 3-chloroindol-6-yl, indol-6-yl or 3-methylindol-6-yl.

15. A compound according to claim 14 wherein Cy is selected from phenyl, 2-chlorophenyl, 2-methoxyphenyl, 4-carbamoylphenyl, pyrid-2-yl, pyrid-4-yl, thien-2-yl, thien-3-yl, furan-2-yl, furan-3-yl, imidazol-2-yl, thiazol-2-yl, thiazol-4-yl, 2-amino-thiazol-4-yl, thiazol-5-yl, naphth-1-yl, isoquinolin-5-yl, isoquinolin-8-yl, quinolin-4-yl, quinolin-5-yl and quinolin-8-yl.

16. A compound according to claim 15 wherein Cy is phenyl.

17. A pharmaceutical composition, which comprises a compound as claimed in claim 1 together with at least one pharmaceutically acceptable carrier or excipient.

18. A method of treatment of a human or non-human animal body to combat a thrombotic disorder selected from venous thrombosis, pulmonary embolism, arterial thrombosis, myocardial ischemia, myocardial infarction and cerebral thrombosis, which comprises administering to said body an effective amount of a compound as claimed in claim 1.

* * * * *